United States Patent [19]

Nakamura et al.

[11] Patent Number: 4,713,317
[45] Date of Patent: Dec. 15, 1987

[54] SILVER HALIDE COLOR PHOTOGRAPHIC MATERIAL

[75] Inventors: Shinichi Nakamura, Tokyo; Keiji Ohbayashi, Hino, both of Japan

[73] Assignee: Konishiroku Photo Industry Co., Ltd., Tokyo, Japan

[21] Appl. No.: 852,375

[22] Filed: Apr. 16, 1986

Related U.S. Application Data

[63] Continuation of Ser. No. 736,559, May 21, 1985, abandoned.

[30] Foreign Application Priority Data

May 22, 1984 [JP] Japan ................................. 50-103273
Sep. 6, 1984 [JP] Japan ................................. 59-187099

[51] Int. Cl.$^4$ ............................ G03C 1/40; G03C 7/32
[52] U.S. Cl. ...................................... 430/551; 430/607
[58] Field of Search ............... 430/551, 546, 543, 607, 430/931, 512

[56] References Cited

U.S. PATENT DOCUMENTS

| | | | |
|---|---|---|---|
| 2,735,765 | 2/1956 | Loria et al. | 430/551 |
| 3,432,300 | 3/1969 | Lesting et al. | 430/551 |
| 3,788,857 | 11/1974 | Van Poucke et al. | 430/546 |
| 4,004,928 | 1/1977 | Miyazawa et al. | 430/551 |
| 4,489,155 | 12/1984 | Sakanoue et al. | 430/551 |
| 4,529,690 | 7/1985 | Ohbayashi et al. | 430/551 |

FOREIGN PATENT DOCUMENTS 0137273 4/1985 European Pat. Off.
3323448 12/1983 Fed. Rep. of Germany.

*Primary Examiner*—Richard L. Schilling
*Attorney, Agent, or Firm*—Jordan B. Bierman

[57] ABSTRACT

A silver halide color photographic material is disclosed which has a support at least one silver halide emulsion layer containing a non-diffusible coupler, wherein a compound of formula (I) is incorporated in either said silver halide emulsion layer or a layer adjacent thereto or both:

$$R_1-O-R_2 \qquad (I)$$

wherein $R_1$ and $R_2$ each represents an alkyl group, a cycloalkyl group or an alkenyl group.

14 Claims, No Drawings

SILVER HALIDE COLOR PHOTOGRAPHIC MATERIAL

This application is a continuation of application Ser. No. 736,559, filed May 21, 1985, now abandoned, which claims the priority of Japanese Application Nos. 103,273/84 and 187,099/84, filed May 22, 1984 and Sept. 6, 1984, respectively.

FIELD OF THE INVENTION

The present invention relates to a silver halide color photographic material having improved dye image keeping quality. More particularly, the invention relates to a silver halide color photographic material which is protected from any undesired color formation (staining) or discoloration in the background or dye image area that may result from exposure to light, moisture and heat.

BACKGROUND OF THE INVENTION

As is well known, the process of producing a color image in a silver halide color photographic material (hereinunder referred to as a color photographic material) comprises developing exposed silver halide grains with an aromatic primary amine compound, and reacting the oxidation product of the aromatic primary amine compound with a coupler to thereby form a dye. In this process, cyan, magenta and yellow dyes are respectively formed by using a phenolic or naphtholic coupler, a 5-pyrazolone, pyrazolinobenzimidazole, pyrazolotriazole, indazolone or cyanoacetylic coupler, and an acylacetamide or dibenzoylmethane coupler.

It is desired that the dye image formed by this process will not change in color or fade after prolonged exposure to light or even if it is left to stand in a hot and humid atmosphere. In order to meet this requirement, proposals have been made to select couplers that are resistant to color change or fading, to use an UV absorber, or to incorporate a compound capable of preventing any color change or fading that results from exposure to light.

However, most of the techniques proposed to date are directed to the prevention or inhibition of the fading that occurs in the dye image as a result of exposure to light, moisture or heat, and very few proposals have been made concerning techniques that are effective in preventing undesired staining in the background. Under these circumstances, color photographic materials are available that produce a dye image having satisfactory resistance to light, moisture and heat but even such photographic materials are not adequately protected from undesired staining in the background. A color photographic product having good protection from color change and fading both in the background and in the image area is desired.

Most of the efforts made so far to prevent or inhibit the undesired staining in the background of a color photographic material depend on incorporating a fairly large amount of an UV absorber in the photographic material. However, using a great amount of UV absorber in a reflection color photographic material is not desired since an undesired color formation occurs in the background. Some UV absorbers lose their resistance to UV rays after the lapse of a certain period of time, accelerated staining occurs in the background. The use of a high content of UV absorber causes other problems: the physical properties of the gelatin coating in the color photographic material are impaired and this leads to reduced hardenability, sweating or even the formation of reticulation.

It is known that the staining of the background that results from exposure to heat and moisture depends largely upon the type of coupler used, but the techniques that are effective in preventing such staining are much fewer than those available for the purpose of preventing or inhibiting the undesired staining in the background that results from exposure to light.

SUMMARY OF THE INVENTION

One object of the present invention is to provide a color photographic material that is protected to an appreciable degree from the undesired staining in the background that may result from exposure to light, moisture and heat.

Another object of the present invention is to provide a color photographic material that is protected from the undesired discoloration in the dye image resulting from exposure to light, moisture and heat and which is also capable of maintaining a good hue in the image for a prolonged period of storage.

These objects of the present invention can be achieved by a silver halide color photographic material that has on a support at least one silver halide emulsion layer containing a non-diffusible coupler, wherein an ether compound of formula (I) incorporated in either said silver halide emulsion layer or a layer adjacent thereto or both (the ether compound is hereunder sometimes collectively referred to as the ether compound of the present invention):

$$R_1-O-R_2 \qquad (I)$$

In formula (I), $R_1$ and $R_2$ each represents an alkyl group, a cycloalkyl group or an alkenyl group.

DETAILED DESCRIPTION OF THE INVENTION

The alkyl group represented by $R_1$ or $R_2$ in formula (I) is preferably an alkyl group having 1–28 carbon atoms, and illustrative alkyl groups include methyl, ethyl, t-butyl, t-octyl, decyl, tetradecyl, octadecyl, docosyl, benzyl and phenethyl.

The cycloalkyl group represented by $R_1$ or $R_2$ in formula (I) is a cycloalkyl group having 5–10 carbon atoms, and illustrative cycloalkyl groups include cyclopentyl, cyclohexyl and adamantyl.

The alkenyl group represented by $R_1$ $R_2$ in formula (I) is preferably an alkenyl group having 2–20 carbon atoms, and illustrative alkenyl groups include vinyl, allyl, octenyl and octadecenyl.

The alkyl group and alkenyl group represented by $R_1$ or $R_2$ may have a substituent and illustrative substituents include the following: alkoxy group (e.g. methoxy, ethoxy, butoxy, octyloxy or octadecyloxy), aryloxy group (e.g. phenoxy), halogen atom (e.g. bromine, chlorine, fluorine), aryl group (e.g. phenyl or naphthyl), hetero cyclic group (e.g. furyl, imidazolyl or s-triazinyl), trialkylsilyl group (e.g. trimethylsilyl or trismethoxyethylsilyl), alkanesulfonyl group (e.g. methanesulfonyl or octanesulfonyl), arylsulfonyl (e.g. benzenesulfonyl or naphthalenesulfonyl), alkylcarbonyloxy (e.g. methylcarbonyloxy or butylcarbonyloxy), hydroxyl group, and alkoxycarbonyl (e.g. methoxycarbonyl, ethoxycarbonyl, or octadecyloxycarbonyl).

The cycloalkyl group represented by $R_1$ or $R_2$ may have a substituent and illustrative substituents include those which are listed above, as well as an alkyl group (e.g. methyl, propyl, butyl, octyl or dodecyl), and an alkenyl group (e.g. allyl, octynyl or octadecenyl).

Preferred examples of the ether compound of the present invention are those represented by the following formula:

$$R_1-O-R_2 \quad (Ia)$$

or $$Ar_1(\underset{R_{171}}{\underset{|}{\overset{R_{170}}{\overset{|}{C}}}})_m-O-(\underset{R_{173}}{\underset{|}{\overset{R_{172}}{\overset{|}{C}}}})_n Ar_2. \quad (Ib)$$

In formula (Ia), $R_1$ represents an alkenyl group and $R_2$ represents an alkyl group, a cycloalkyl group or an alkenyl group. In formula (Ib), $R_{170}$, $R_{171}$, $R_{172}$ and $R_{173}$ each represent a hydrogen atom, an alkyl group or an aryl group; $Ar_1$ and $Ar_2$ each represent an aryl group, m and n each represent an integer of 1 or 2.

The alkyl group represented by $R_{170}$, $R_{171}$, $R_{172}$ and $R_{173}$ in formula (Ib) is preferably an alkyl group having 1-8 carbon atoms, and illustrative preferred alkyl groups include methyl, ethyl, and i-propyl. A specific example of the aryl group represented by $R_{170}$–$R_{173}$ is phenyl. A hydrogen atom is preferred as each of $R_{170}$–$R_{173}$.

Specific examples of the aryl group represented by $Ar_1$ and $Ar_2$ in formula (Ib) include phenyl, p-methylphenyl and p-n-butoxyphenyl.

Illustrative examples of the ether compounds of the present invention are listed below.

Illustrative ether compounds:

(1) n-$C_8H_{17}$—O—$C_8H_{17}$(n)
(2) n-$C_9H_{19}$—O—$C_9H_{19}$(n)
(3) n-$C_{10}H_{21}$—O—$C_{10}H_{21}$(n)
(4) n-$C_{12}H_{25}$—O—$C_{12}H_{25}$(n)
(5) n-$C_{14}H_{29}$—O—$C_{14}H_{29}$(n)
(6) n-$C_{16}H_{33}$—O—$C_{16}H_{33}$(n)
(7) n-$C_{18}H_{37}$—O—$C_{18}H_{37}$(n)
(8) t-$C_4H_9$—O—$C_{18}H_{37}$(n)
(9) n-$C_8H_{17}$—O—$CH_2CH_2$—O—$C_8H_{17}$(n)
(10) n-$C_{14}H_{29}$—O—$CH_2CH_2$—O—$C_{14}H_{29}$(n)
(11) n-$C_{12}H_{25}$—O—$CH_2CH_2$—O—$C_8H_{17}$(n)
(12) $CH_2$=$CHCH_2$—O—$C_{10}H_{21}$(n)
(13) $CH_2$=$CHCH_2$—O—$C_{12}H_{25}$(n)
(14) $CH_2$=$CHCH_2$—O—$C_{14}H_{29}$(n)
(15) $CH_2$=$CHCH_2$—O—$C_{18}H_{37}$(n)
(16) $CH_2$=$CH$—$CH_2$—O—$C_{18}H_{35}$(n)

(17) $CH_2$=$CH$—$CH_2$—O—$C_{20}H_{41}$(n)

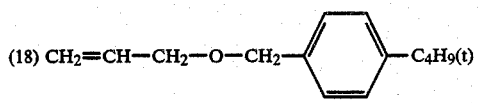
(18) $CH_2$=$CH$—$CH_2$—O—$CH_2$—⟨phenyl⟩—$C_4H_9$(t)

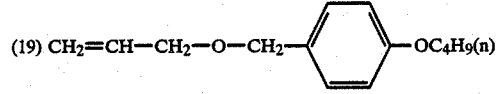
(19) $CH_2$=$CH$—$CH_2$—O—$CH_2$—⟨phenyl⟩—$OC_4H_9$(n)

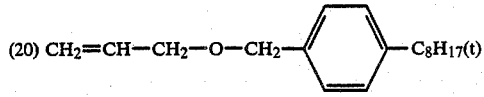
(20) $CH_2$=$CH$—$CH_2$—O—$CH_2$—⟨phenyl⟩—$C_8H_{17}$(t)

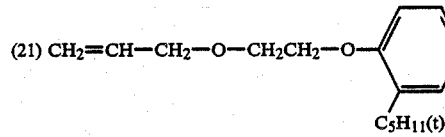
(21) $CH_2$=$CH$—$CH_2$—O—$CH_2CH_2$—O—⟨phenyl with two $C_5H_{11}(t)$ substituents⟩

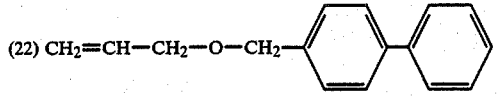
(22) $CH_2$=$CH$—$CH_2$—O—$CH_2$—⟨biphenyl⟩

(23) $CH_2$=$CH$—$CH_2$—O—$CH_2CH_2CH_2$—$OCOC_{18}H_{37}$(n)

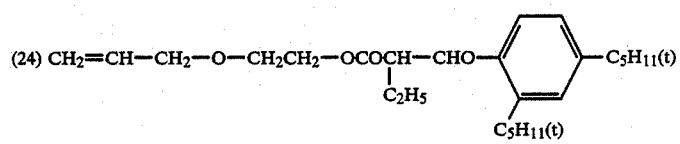
(24) $CH_2$=$CH$—$CH_2$—O—$CH_2CH_2$—$OCOCH$($C_2H_5$)—$CHO$—⟨phenyl with two $C_5H_{11}(t)$⟩

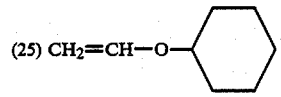
(25) $CH_2$=$CH$—O—⟨cyclohexyl⟩
(26) $CH_2$=$CH$—O—$C_{10}H_{21}$(n)

(27) $CH_2$=$CH$—O—$C_{12}H_{25}$(n)
(28) $CH_2$=$CH$—O—$C_{14}H_{29}$(n)

(29) $CH_2$=$CH$—O—$C_{18}H_{37}$(n)
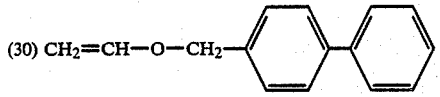
(30) $CH_2$=$CH$—O—$CH_2$—⟨biphenyl⟩

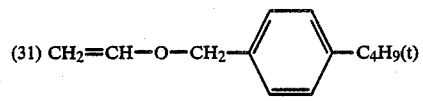
(31) $CH_2$=$CH$—O—$CH_2$—⟨phenyl⟩—$C_4H_9$(t)

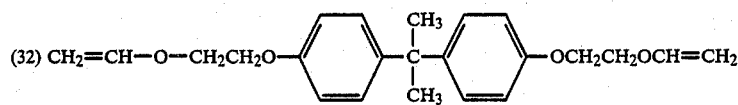
(32) $CH_2$=$CH$—O—$CH_2CH_2O$—⟨phenyl⟩—$C(CH_3)_2$—⟨phenyl⟩—$OCH_2CH_2OCH$=$CH_2$ -continued
Illustrative ether compounds:
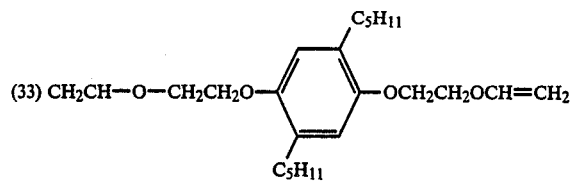
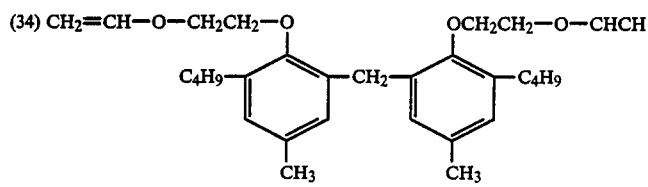
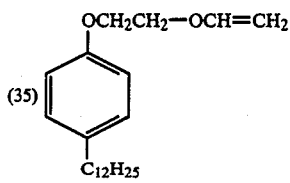
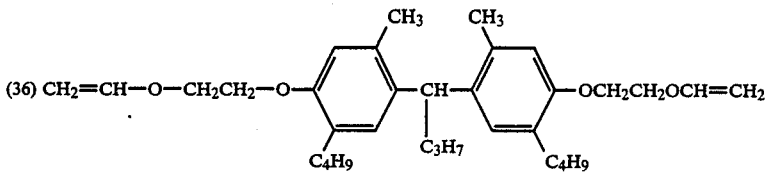
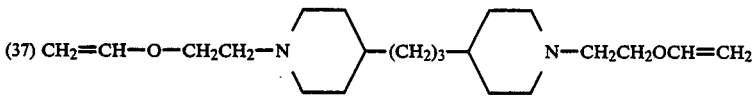
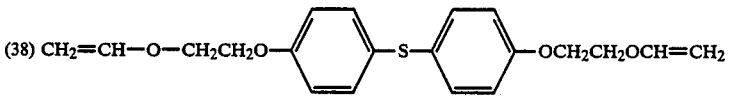
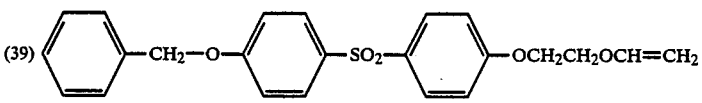
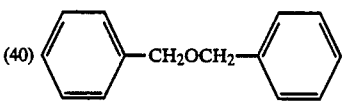
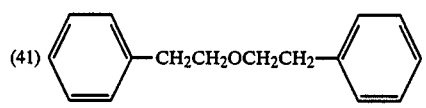
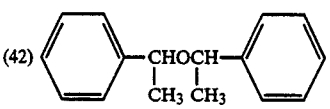
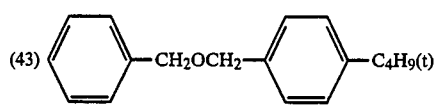
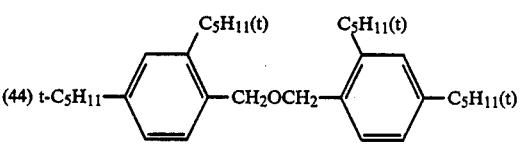
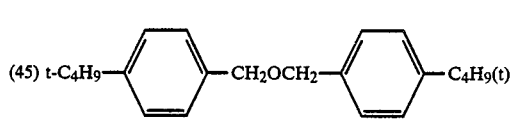
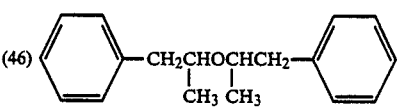
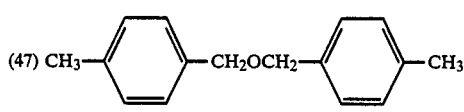

-continued
Illustrative ether compounds:
(48) 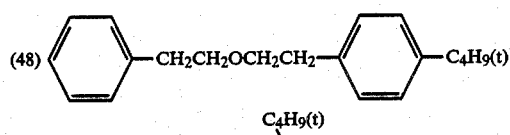
(49) 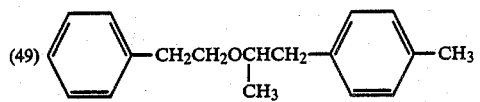
(50) 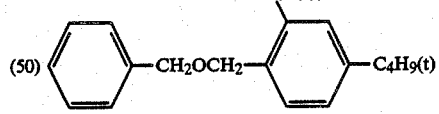
(51) n-C$_4$H$_9$O— 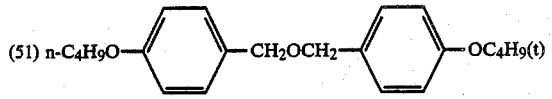
(52) HO— 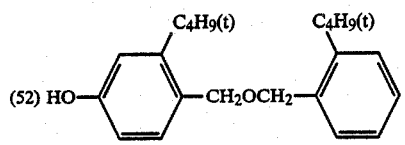
(53) CH$_3$— 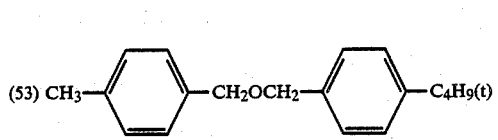
(54) CH$_3$— 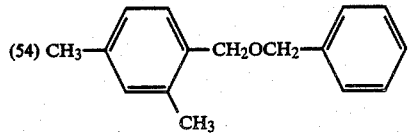
(55) CH$_3$— 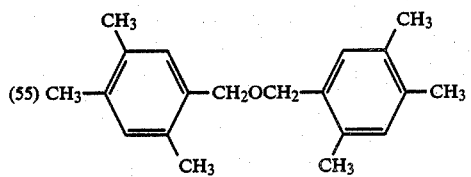
(56) 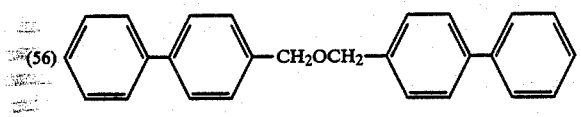
(57) CH$_3$— 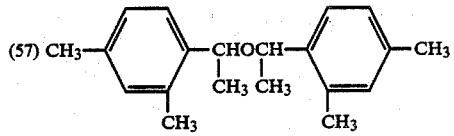
(58) sec-C$_6$H$_{13}$— 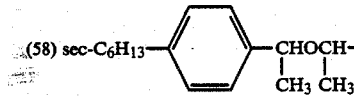 —C$_6$H$_{13}$(sec)
(59) t-C$_8$H$_{17}$— 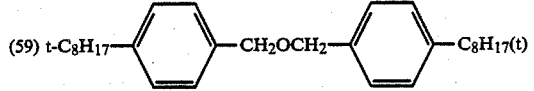 —C$_8$H$_{17}$(t)
(60) H— 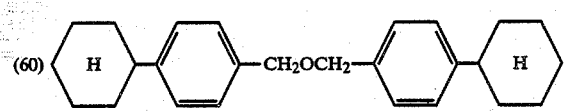 —H
(61) 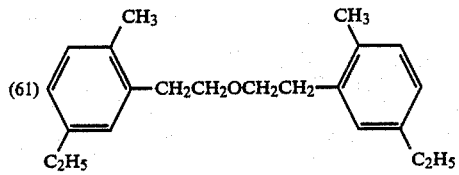
(62) C$_{12}$H$_{25}$CONH— 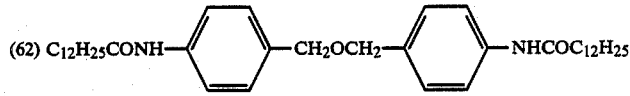 —NHCOC$_{12}$H$_{25}$
(63) C$_3$H$_7$O— 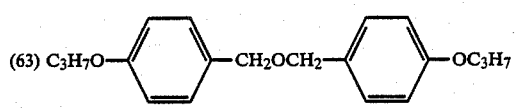 —OC$_3$H$_7$
(64) CH$_3$— 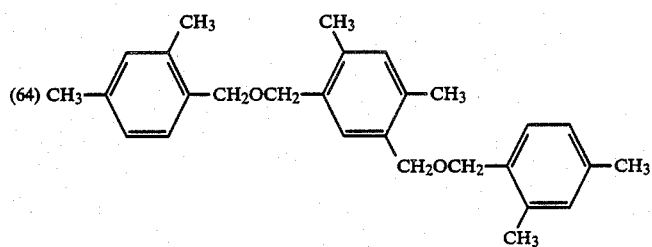

-continued
Illustrative ether compounds:

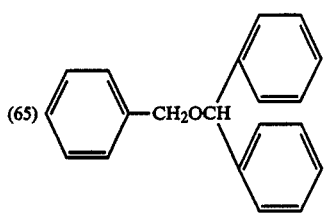 (65)

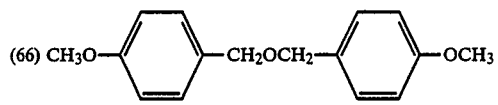 (66)

Some of the ether compounds of the present invention listed above are commercially available but all of them can readily be synthesized by known methods, such as the dehydration of aliphatic alcohols, and Williamson's synthesis wherein a sodium salt of aliphatic alcohols, ethylene glycol monoalkyl ether, ethylene glycol or propylene glycol is reacted with an alkyl halide. For details of these methods, see "Synthesis of Organic Compounds I", vol. 19, Course in Experimental Chemistry, p. 176, 1957, edited by the Chemical Society of Japan and published by Maruzen, and "Aliphatic Compounds I" vol. 2 of Great Organic Chemistry, p. 321, 1957, published by Asakura Shoten.

Compounds (12) and (24) of formula (Ia) may be synthesized by one of the following three methods: (1) 1,2dibromoethane is reacted with an aliphatic alcohol to remove bromic acid and produce 2-bromoethylalkyl ether, which is then subjected to a reaction in an alkali solution for removing bromic acid, thereby producing vinyl ether; (2) an allyl alcohol is reacted with an alkyl halide to remove a corresponding hydrogen halide; and (3) phenol or a hydroquinone compound is reacted with chloroethylvinyl ether to remove the corresponding hydrochloric acid. For details of these methods, see "Synthesis of Organic Compounds I", supra, pp. 1-31, and "Aliphatic Compounds I", supra, pp. 339-343.

Ether compounds of formula (Ib) in accordance with the present invention may be synthesized by the following illustrative methods.

Synthesis I (Compound 45)

A 100-ml egg-shaped flask was charged with 25 g of p-t-butylbenzyl alcohol and 0.3 g of sulfamic acid and agitated at 150° C. on an oil bath under reduced pressure. After about one hour of the heating, globules of sulfamic acid/water mixture adhered to the bottom of the flask and was separated from the supernatant. These globules were washed out with ethyl acetate and added to the supernatant. The mixture was concentrated under reduced pressure and distilled at 160°-175° C./0.07 mmHg so as to obtain 6.2 g of a colorless liquid material. The results of elemental, NMR and IR analyses supported that this material had the structure of the end compound.

Synthesis 2 (Compound 55)

A mixture of 1,2,4-trimethylbenzene (240 g), formalin (178 g) and conc. HCl (1,250 ml) was heated at 60°-65° C. for 6 hours. After cooling, the product was subjected to extraction with petroleum and the extract was distilled. Fractions having boiling points of 40°-105° C. were collected (yield of 2,4,5-trimethylbenzyl chloride: 264 g).

A mixture of 2,4,5-trimethylbenzyl chloride (16.9 g), anhydrous sodium carbonate (11.0 g) and pure water (100 ml) was heated under reflux for ca. 12 hours. After cooling, the solid product was filtered off and the filtrate was concentrated with heat, followed by recrystallization from chloroform. The obtained material had a yield of 4.8 g and the results of NMR, IR and elemental analyses supported that this material had the structure of the end compound.

The ether compounds of the present invention are incorporated in a silver halide emulsion layer and/or a layer adjacent thereto in a color photographic material. The ether compounds of the present invention may be incorporated in either one of these layers; alternatively, the compounds may be present simultaneously in two or more layers including these layers. Preferably, the ether compounds of the present invention are contained in a silver halide emulsion layer. The silver halide emulsion layer may be composed of a plurality of layers that are sensitive to substantially the same color but which have different sensitivities to light. The ether compounds of the present invention may be incorporated in one or more of such silver halide emulsion layers that have different sensitivities to light.

The ether compounds of the present invention are generally oil-soluble and are preferably incorporated in a silver halide emulsion layer or a layer adjacent thereto in accordance with any of the methods shown in U.S. Pat. Nos. 2,322,027, 2,801,170, 2,801,171, 2,272,191 and 2,304,940; namely, the ether compounds of the present invention are dissolved in high-boiling organic solvents, optionally in combination with low-boiling organic solvents, and the resulting solution is dispersed in a solution of a hydrophilic colloidal substance such as gelatin. If desired, photographic additives such as a coupler, a hydroquinone derivative, an image stabilizer, and an UV absorber may also be incorporated in the colloidal solution together with the ether compounds of the present invention. The ether compounds of the present invention may be used either alone or in combination with themselves.

The methods of addition of the ether compounds of the present invention are described below in detail. First, one or more of the ether compounds of the present invention, optionally together with photographic additives such as a coupler, a hydroquinone derivative, an image stabilizer and an UV absorber, are dissolved in high-boiling organic solvents such as organic acid amides, carbamates, esters, ketones, hydrocarbons and urea derivatives, optionally in combination with low-boiling organic solvents such as ethyl acetate, butyl acetate, cyclohexanol, cyclohexane and tetrahydrofuran (such high-boiling or low-boiling organic solvents may be used either alone or in admixture of themselves). Then, the resulting solution is mixed with an aqueous solution containing an anionic surfactant such as alkylbenzenesulfonic acid, alkylnaphthalenesulfonic acid or sodium alkylsulfosuccinate and/or a nonionic surfactant such as sorbitansesquioleate ester or sorbitanmonolaurate ester. The mixture is then emulsified by a highspeed rotary mixer, colloid mill or an ultrasonic disperser. The resulting dispersion is added to a hydrophilic colloidal solution.

The hydrophilic colloidal solution thus containing the ester compounds of the present invention (the solution may also contain one or more of the silver halides described below in order to prepare a silver halide emulsion) may be coated onto a photographic support by a variety of known methods so as to produce a silver halide color photographic material.

If the ether compounds of the present invention are incorporated in a light-sensitive silver halide emulsion layer, they are preferably present in an amount ranging from 5 to 200 wt % of the coupler in the emulsion layer, with the range of 10–100 wt % being particularly preferred. If the ether compounds of the present invention are incorporated in two or more silver halide emulsion layers, the above defined range need be satisfied by the sum of the amounts of the ether compounds in the respective emultion layers. If the ether compounds of the present invention are incorporated in a non-sensitive hydrophilic colloidal layer adjacent to the light-sensitive silver halide emulsion layer, the contents of the ether compounds range from 0.02 to 2 g, preferably from 0.05 to 1 g, per square meter of the color photographic material.

The object of the present invention can be achieved irrespective of whether the ether compounds shown above are combined with cyan couplers, yellow couplers or magenta couplers. For the purpose of preventing the undesired color formation in the background that may result from exposure to light, heat or moisture, the ether compounds may most effectively be combined with magenta couplers. Magenta couplers preferably used in the present invention are 5-pyrazolones and pyrazolinobenzotriazoles. Particularly preferred are the magenta couplers represented by the following formulas (II) and (III):

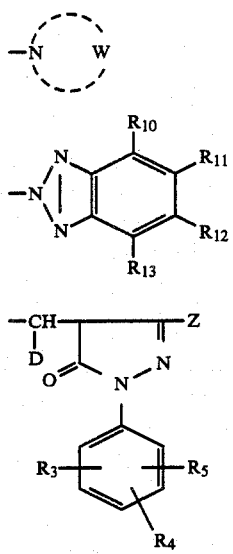

wherein $R_3$, $R_4$ and $R_5$ each independently represent a hydrogen atom, a halogen atom (e.g. chloride or bromine), an alkyl group or an alkoxy group: Z is an alkyl group, —NH—L,—NHCO—L, —NHCOHN—L or -13 $OR_6$ (wherein L is a phenyl group or which may have a substituent, and $R_6$ is an alkyl group or an aryl group, both of which may have a substituent); Q is a hydrogen atom or a group capable of leaving upon coupling with the oxidation product of a color developing agent, such as a halogen atom (e.g. chlorine or bromine), —$COR_7$, —$OR_8$, —$OCOR_9$, —$OSO_2R_9$, —$SR_9$,

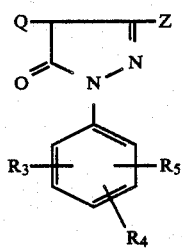

(D is a hydrogen atom, an alkyl group or a phenyl group; Z and $R_{3-R_5}$ are the same as defined for formula (II), wherein $R_7$ is an alkyl group, an alkoxy group, an aryl group or an aryloxy group, each of which groups may have a substituent; $R_8$ is an alkyl group, an alkenyl group, an aryl group or a trialkylsilyl group, each of which groups may have a substituent; $R_9$ is an alkyl group, an aryl group or a heterocyclic group, each of which groups may have a substituent; $R_{10}$–$R_{13}$ each independently represent a hydrogen atom, a halogen atom (e.g. chlorine or bromine) or an alkyl group which may have a substituent; W is a group of the non-metallic atoms necessary for forming a 5-membered ring together with the nitrogen atom to which they are bonded.

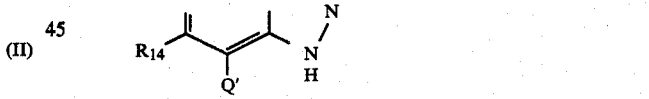

wherein $R_{14}$ and $R_{15}$ each independently represent a hydrogen atom, an alkyl group, an aryl group, a heterocyclic group, an amino group, an acylamino group, a hydroxyl group, an alkoxy group, a carboxyl group or an esterified carboxy group, among which the alkyl, aryl, heterocyclic and alkoxy groups may have a substituent; at least one of $R_{14}$ and $R_{15}$ is a group other than the hydrogen atom; Q' is a hydrogen atom or a group capable of leaving upon coupling with the oxidized product of a color developing agent, such as —$SO_3H$, —COOH, $R_{16}$—O—, $R_{16}$—S— or —N=N—$R_{17}$ (wherein $R_{16}$ is an aryl group which a substituent; $R_{17}$ is an amino group, an acyloxy group, a sulfonyloxy group, a thiocyano group, an imide group or a benzotriazolyl group, each of which groups may have a substituent).

Illustrative but non-limiting examples of the magenta couplers of formulas (II) and (III) that may advantageously be used in the present invention are listed below.

Illustrative magenta couplers:
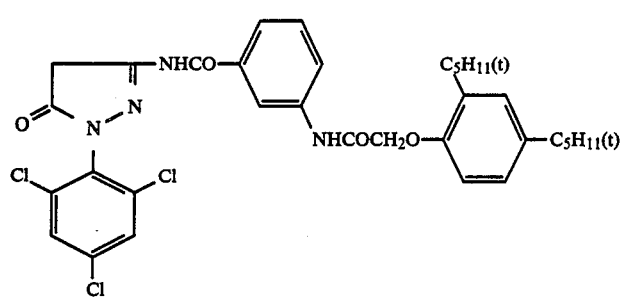
(M-1)
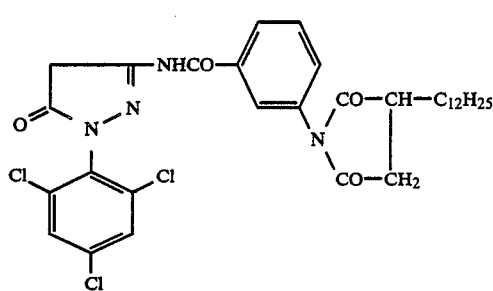
(M-2)
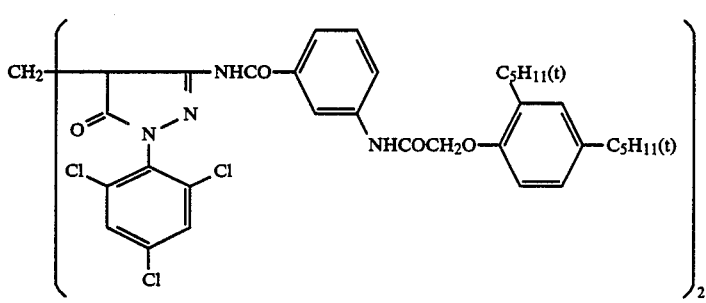
(M-3)
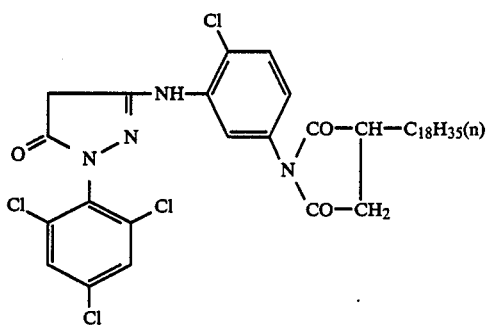
(M-4)
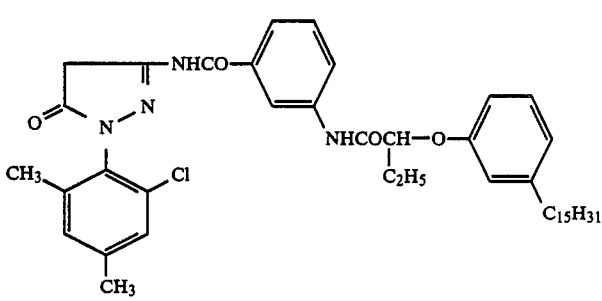
(M-5)

-continued
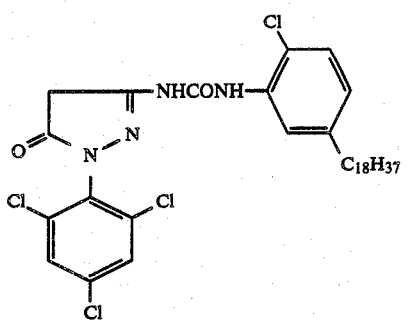
(M-6)
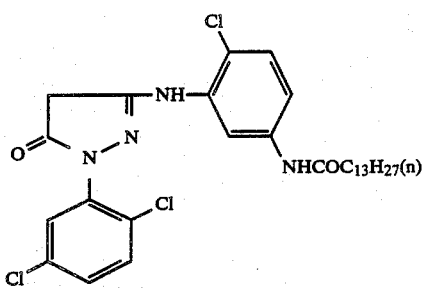
(M-7)
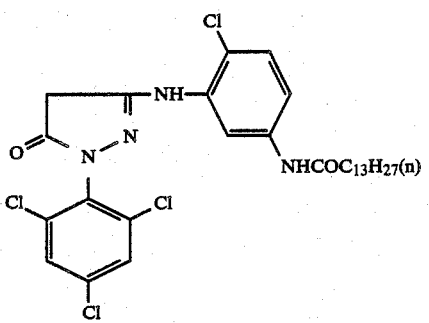
(M-8)
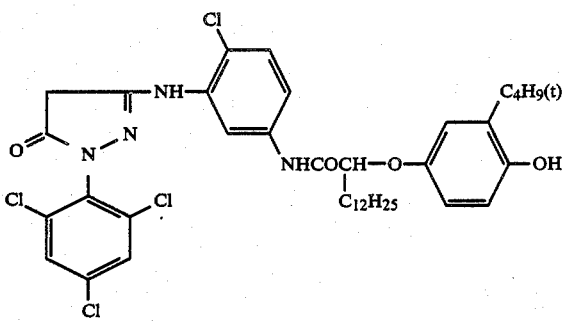
(M-9)
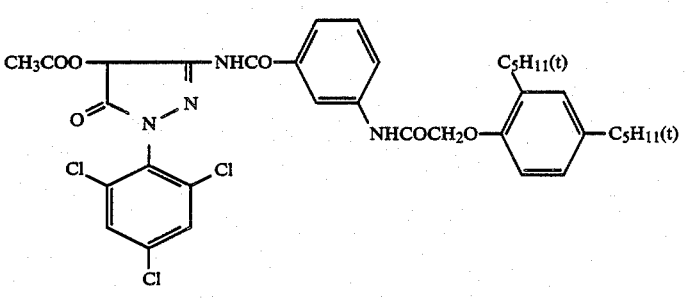
(M-10)

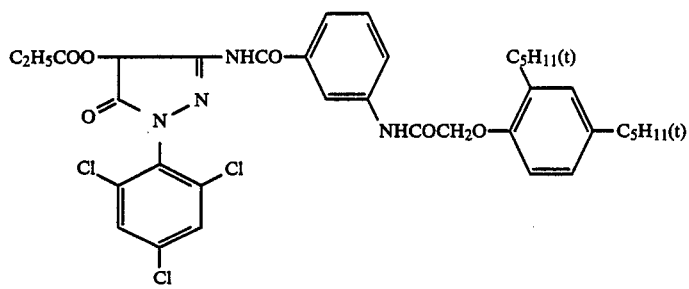
(M-11)
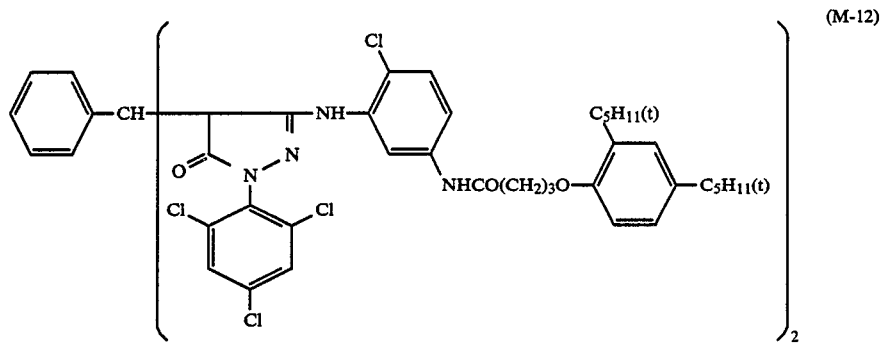
(M-12)
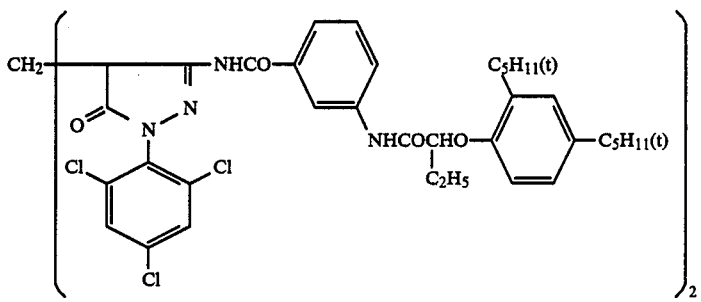
(M-13)
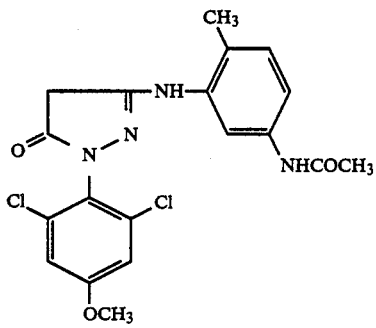
(M-14)
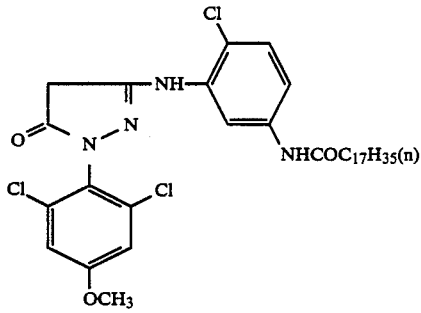
(M-15)

(M-16)
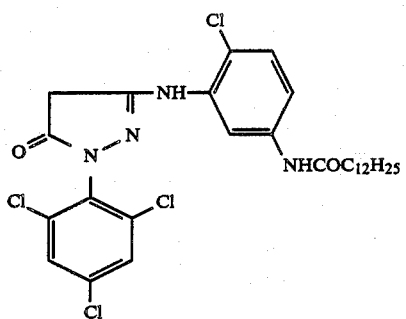
(M-17)
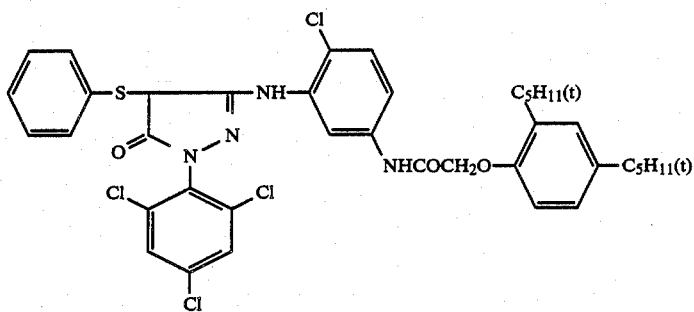
(M-18)
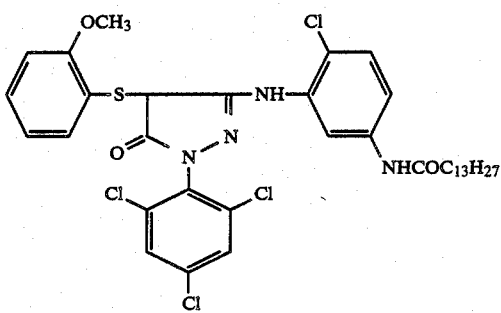
(M-19)
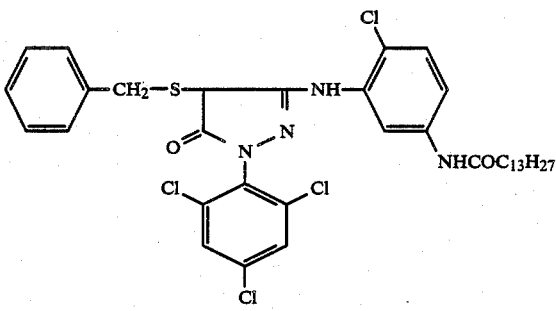
(M-20)
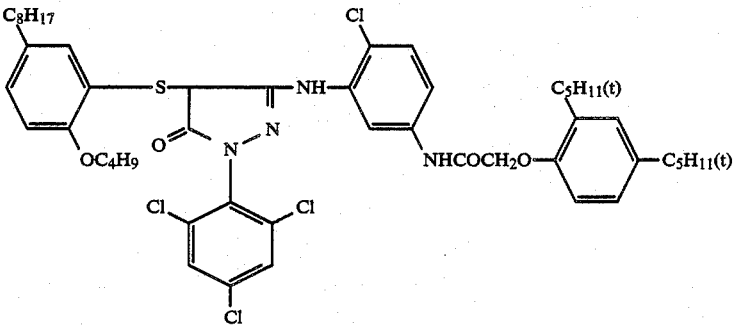

-continued
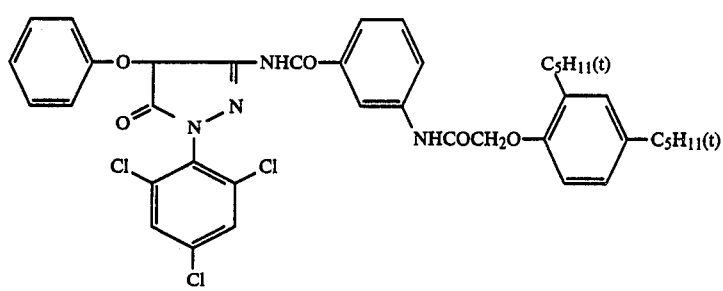
(M-21)
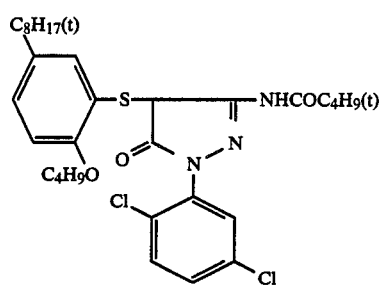
(M-22)
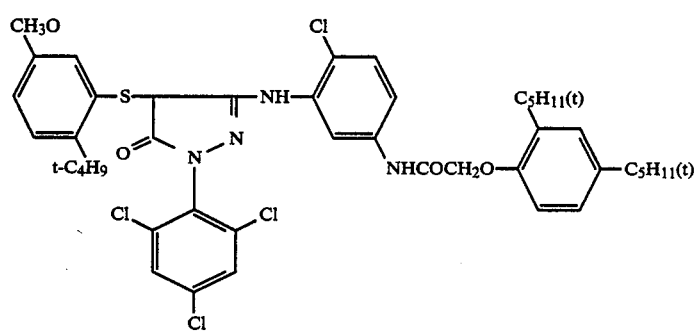
(M-23)
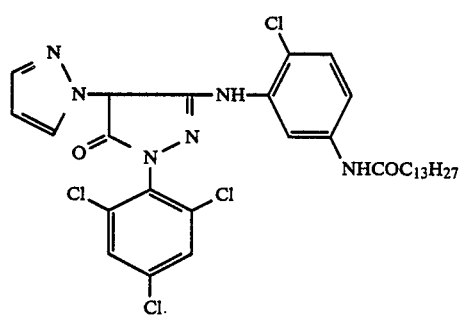
(M-24)
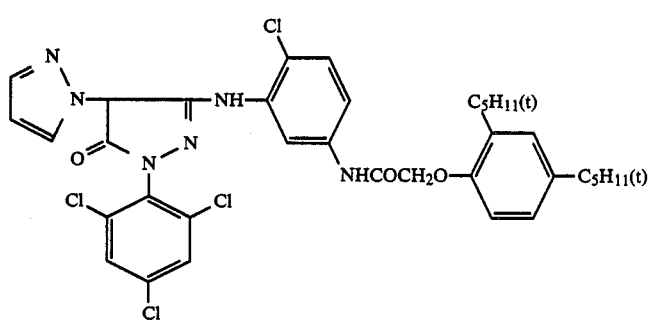
(M-25)

-continued
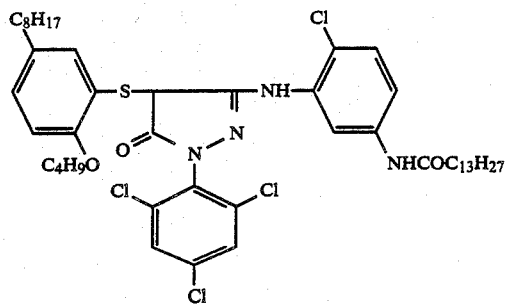 (M-26)
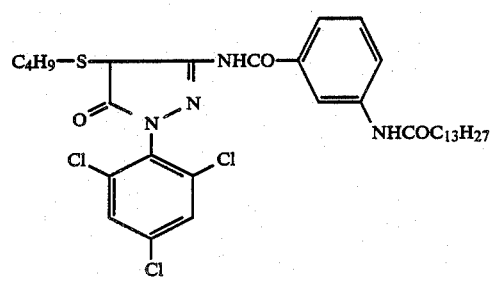 (M-27)
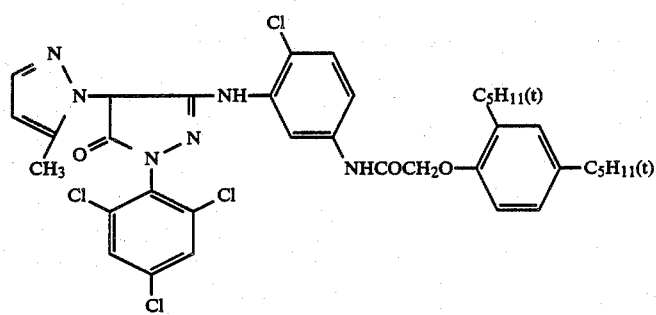 (M-28)
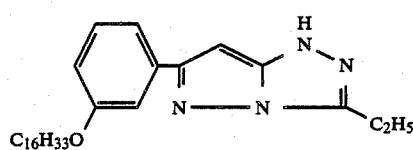 (M-29)
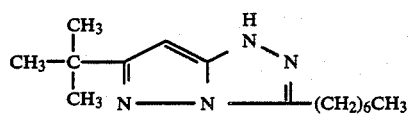 (M-30)
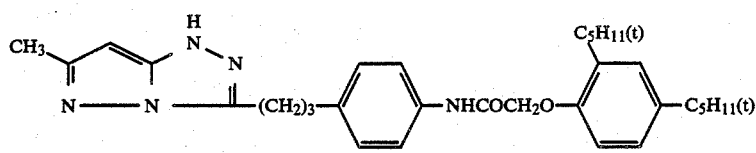 (M-31)
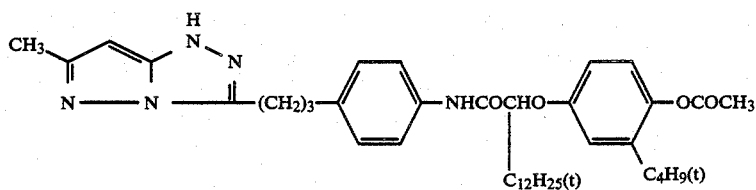 (M-32)

-continued

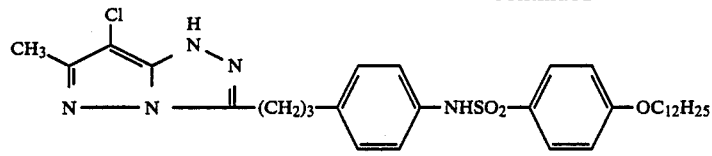
(M-33)

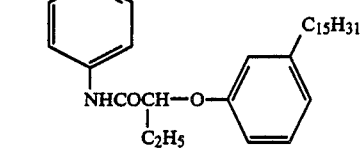
(M-34)

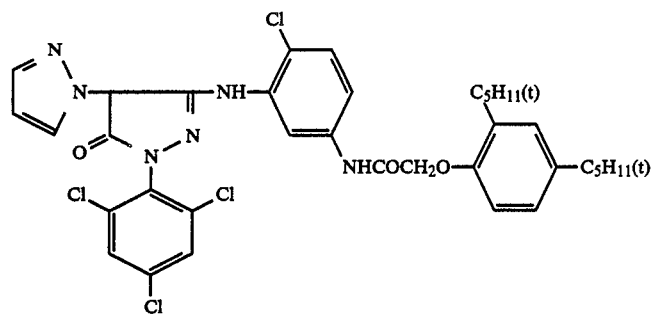
(M-35)

The magenta couplers listed above may be used either alone or in combination with themselves. They may also be used in combination with known magenta couplers based on pyrazolinobenzoimidazoles and indazolones.

The objectives in accordance with the present invention for preventing or inhibiting the occurrence of undesired color formation in the background or color change in the dye image area that may result from exposure to light, heat or moisture may most effectively be achieved when the ether compounds of the present invention are incorporated in the layer containing the magenta coupler shown above or a layer adjacent thereto.

The color photographic material of the present invention may contain yellow- and cyan-dye forming couplers. Suitable yellow-dye forming couplers are benzoylacetanilide compounds, pivaloylacetanilide compounds and two-equivalent couplers wherein the carbon atom on the coupling site is replaced by a split-off group, or a substituent that is capable of leaving upon coupling reaction. Suitable cyan-dye forming couplers are phenol compounds, naphthol compounds, pyrazoloquinazolone compounds and two-equivalent couplers having a split-off group.

Illustrative yellow-dye forming couplers are shown in U.S. Pat. Nos. 2,778,658, 2,875,057, 2,908,573, 2,908,513, 3,227,155, 3,227,550, 3,253,924, 3,265,506, 3,277,155, 3,341,331, 3,369,895, 3,384,657, 3,408,194, 3,415,652, 3,447,928, 3,551,155, 3,582,322 and 3,725,072; German Pat. Nos. 1,547,868, 2,057,941, 2,162,899, 2,163,812, 2,213,461, 2,219,917, 2,261,361 and 2,263,875; Japanese Patent Publication No. 13576/74, as well as Unexamined Published Japanese Patent Application Nos. 29432/73, 66834/73, 10736/74, 122335/74, 28834/75, 132926/75, 144240/80 and 87041/81.

Illustrative cyan-dye forming couplers are found in U.S. Pat. Nos. 2,369,929, 2,423,730, 2,434,272, 2,474,293, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,563, 3,516,831, 3,560,212, 3,582,322, 3,583,971, 3,591,383, 3,619,196, 3,632,347, 3,652,286, 3,737,326, 3,758,308, 3,779,768 and 3,839,044; German Pat. Nos. 2,163,811 and 2,207,468; Japanese Patent Publication Nos. 7563/64 and 28836/70; and Unexamined Published Japanese Patent Application Nos. 37425/72, 10135/75, 25228/75, 12038/75, 117422/75, 130441/75, 109630/78, 32071/80, 63537/80, 1938/81, 13643/81, 29235/81, 65134/81, 04333/81; and Research Disclosure, No. 14853, 1976.

As already mentioned, the ether compounds of the present invention are incorporated in a color photographic material with the aid of high-boiling organic solvents, and preferred high-boiling organic solvents are those which are immiscible with water and have boiling points not lower than ca. 170° C. Specific examples of the preferred high-boiling organic solvents include the following: phthalates (e.g. dimethyl phthalate, dibutyl phthalate, dioctyl phthalate, diallyl phthalate, dinonyl phthalate, dilauryl phthalate, dibenzyl phthalate and diphenyl phthalate), phosphates (e.g. diphenyl phosphate, tricresyl phosphate, triphenyl phosphate, dioctyl-butyl phosphate, trihexyl phosphate and trioctyl phosphate), citrates (e.g. acetylcitric acid tributylate and tributyl citrate), benzoate esters (e.g. butyl benzoate and octyl benzoate), alkylamides (e.g. diethyl laurylamide), sebacate esters (e.g. diethylhexyl sebacate), stearate esters (e.g. butyl stearate), maleate esters (e.g. dinonyl maleate), succinate esters (diethyl succinate), adipate esters (e.g. dioctyl adipate) and pyrrolidone (e.g. N-dodecylpyrrolidone).

Low-boiling (ca. 30–150° C.) organic solvents may be used in combination with such high-boiling organic solvents. Illustrative low-boiling organic solvents include lower acetylacetates (e.g. ethyl acetate, butyl acetate and β-ethoxyethyl acetate), butyl alcohol, methyl isobutyl ketone, chloroform, hexanone, cyclohexane, ethylene glycol, acetone, ethanol, dioxane and dimethylformamide.

As already mentioned, the ether compounds of the present invention are preferably incorporated in a silver halide color photographic material by dissolving them in high-boiling organic solvents together with photographic couplers.

The color photographic material in accordance with the present invention may incorporate anti-discoloration agents together with the ether compounds of the present invention. Particularly preferred anti-discoloration agents are those represented by the following formulas (IV), (V), (VI) and (VII).

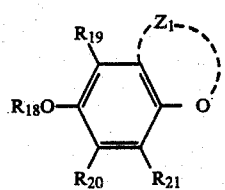
(IV)

wherein $R_{18}$ is a hydrogen atom, an alkyl group of 1–18 carbon atoms (e.g. methyl, isopropyl, n-butyl, n-octyl, n-dodecyl or benzyl), an aryl group (e.g. phenyl), an alkenyl group (e.g. allyl), a cycloalkyl group (e.g. cyclohexyl), a heterocyclic group (e.g. S-triazonyl), a trialkylsilyl group (e.g. trimethylsilyl), an alkanesulfonyl group of 1–20 carbon atoms (e.g. methanesulfonyl, octanesulfonyl or benzylsulfonyl), an arylsulfonyl group (e.g. benzenesulfonyl or naphthalenesulfonyl), —CO—V or —SO$_2$—V, wherein V is an alkyl group of 1–20 carbon atoms (e.g. methyl, t-butyl, cyclohexyl, octyl, dodecyl or benzyl), an aryl group (e.g. phenyl or p-methylphenyl), an alkoxy group of 1–20 carbon atoms (e.g. methoxy, t-butoxy, dodecyloxy or benzyloxy), an aryloxy group (e.g. phenoxy), an alkyloxycarbonyl group (e.g. ethoxycarbonyl, t-butoxycarbonyl or benzyloxycarbonyl) or an aryloxycarbonyl group (e.g. phenoxycarbonyl); preferred examples of $R_{18}$ are a hydrogen atom and an alkyl group; $R_{19}$, $R_{20}$ and $R_{21}$ are each a hydrogen atom, an alkyl group of 1–20 carbon atoms (e.g. methyl, t-butyl, cyclopentyl, octyl, dodecyl or benzyl), an alkoxy group of 1–20 carbon atoms (e.g. methoxy, t-butoxy or octadecyloxy), an aryl group (e.g. phenyl), an aryloxy group (e.g. phenoxy or p-methylphenoxy), or an alkenyl group (e.g. allyl); preferred examples of $R_{19}$, $R_{20}$ and $R_{21}$ are respectively a hydrogen atom, an alkyl group and a hydrogen atom; $Z_1$ is a group of non metallic atoms necessary to form a 5 or 6 membered ring, said non metallic group optionally having a substituent.

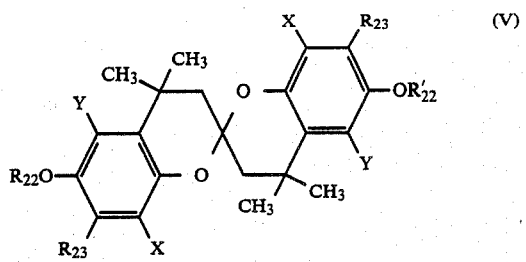

wherein $R_{22}$ and $R'_{22}$ which may be the same or different are each a hydrogen atom, an alkyl group of 1–20 carbon atoms (e.g. methyl, ethyl, t-butyl, n-octyl or n-octadecyl), an alkenyl group (e.g. allyl or octenyl), a cycloalkyl group (e.g. cyclohexyl), an aryl group (e.g. phenyl or p-methylphenyl), a hetero-cyclic group (e.g. imidazolyl or furyl), —CO—V', —SO$_2$—V' or —CONH—V' wherein V' has the same meaning as V defined for formula (IV); $R_{23}$ is an alkyl group of 1–20 carbon atoms (e.g. methyl, ethyl, n-propyl, i-amino, n-octyl, n-dodecyl or n-octadecyl), an alkenyl group of 2–20 carbon atoms (e.g. allyl, octenyl or oleyl), an aryl group (e.g. phenyl), an alkoxy group of 1–20 carbon atoms (e.g. methoxy, t-butoxy or n-dodecyloxy), or an aryloxy group (e.g. phenoxy); when both $R_{22}$ or $R'_{22}$ and $R_{23}$ are an alkyl group, $R_{22}$ or $R'_{22}$ and $R_{23}$ may be fused to form a 5- to 7-membered ring; a preferred example of $R_{23}$ is an alkyl group; X and Y each represent a hydrogen atom, a halogen atom (e.g. chlorine, fluorine or bromine), an alkyl group of 1–20 carbon atoms (e.g. methyl, ethyl, i-propyl, t-butyl, heptyl, dodecyl or benzyl), an alkoxy group of 1–20 carbon atoms (e.g. methoxy, ethoxy, n-butoxy or dodecyloxy), an alkenyl group (e.g. allyl or octenyl), an aryl group (e.g. phenyl) or an aryloxy group (e.g. phenoxy); X and Y are preferably a hydrogen atom.

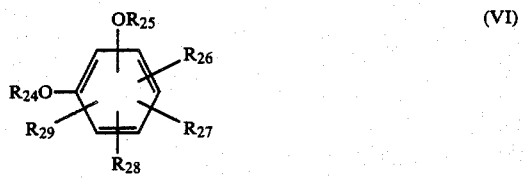

wherein $R_{24}$ and $R_{25}$ are each an alkyl group of 1–20 carbon atoms (e.g. methyl, ethyl, t-butyl, n-octyl, n-decyl, n-octadecyl, benzyl- or phenethyl), an alkenyl group of 1–20 carbon atoms (e.g. allyl, octenyl, or oleyl), a cycloalkyl group (e.g. cyclohexyl), an aryl group (e.g. phenyl), a trialkylsilyl group (e.g. trimethylsilyl) or a heterocyclic group (e.g. imidazolyl, furyl or triazinyl); when —OR$_{25}$ is in the position ortho to —OR$_{24}$, $R_{24}$ and $R_{25}$ may be fused to form a 5- or 6-membered ring; both $R_{24}$ and $R_{25}$ are preferably an alkyl, cycloalkyl or alkenyl; $R_{26}$, $R_{27}$, $R_{28}$ and $R_{29}$ are each a hydrogan atom, a halogen atom (e.g. chlorine, fluorine or bromine), an alkyl group of 1–20 carbon atoms (e.g. methyl, ethyl, t-butyl, i-amyl, t-octyl or n-octadecyl), an alkenyl group of 2–20 carbon atoms (e.g. allyl, octenyl or oleyl), a cycloalkyl group (e.g. cyclohexyl), an aryl group (e.g. phenyl), an acyl group of 2–12 carbon atoms (e.g. acetyl benzoyl or octanoyl), an acylamino group of 2–12 carbon atoms (e.g. acetylamino, octanoylamino or benzoylamino), an alkylamino group of 1–20 carbon atoms (e.g. methylamino, diethylamino or di-n-octylamino), an alkoxycarbonyl group of 2–20 carbon atoms (e.g. methoxycarbonyl or n-nonylcarbonyl) or a sulfonamido group (e.g. methylsulfonamido, octylsulfonamido or phenylsulfonamido), provided that $R_{26}$, $R_{27}$, $R_{28}$ and $R_{29}$ are not a hydrogen atom at the same time.

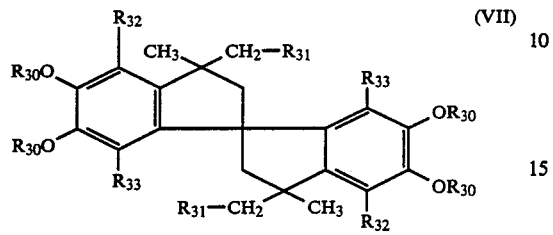

(VII)

wherein $R_{30}$ is an alkyl group of 1–20 carbon atoms (e.g. methyl, ethyl, i-propyl, n-octyl, n-dodecyl or benzyl), an alkenyl group of 2–20 carbon atoms (e.g. allyl, octenyl or oleyl), an aryl group (e.g. phenyl), a heterocyclic group (e.g. pyrimidyl or tetrahydropyranyl), —$COR'_{30}$, —$SO_2R'_{30}$ or —$CONHR'_{30}$, wherein $R'_{30}$ is an alkyl group of 1–20 carbon atoms (e.g. methyl, ethyl, i-propyl, n-octyl, n-dodecyl or benzoyl), an alkenyl group of 1–20 carbon atoms (e.g. allyl, octenyl or oleyl), an aryl group (e.g. phenyl); when $R_{30}$ is an alkyl group, two adjacent $R_{30}$ may be fused to form a 5- or 6-membered ring; $R_{30}$ is preferably an alkyl group; $R_{31}$ is a hydrogen atom, an alkyl group of 1–8 carbon atoms (e.g. methyl, ethyl, n-butyl or benzyl), an alkenyl group of 3–8 carbon atoms (e.g. allyl or octenyl), or an aryl group (e.g. phenyl); $R_{31}$ is preferably a hydrogen atom or an alkyl group; $R_{32}$ and $R_{33}$ are each a hydrogen atom, a halogen atom (e.g. chlorine, fluorine or bromine), an alkyl group of 1–20 carbon atoms (e.g. methyl, ethyl, n-octyl, n-dodecyl or benzyl), an alkenyl group of 2–20 carbon atoms (e.g. allyl, octenyl or oleyl) or an alkoxy group of 1–20 carbon atoms (e.g. methoxy, ethoxy or benzyloxy); $R_{32}$ and $R_{33}$ are preferably a hydrogen atom, an alkyl group or an alkoxy group.

Illustrative examples of the compounds of formula (IV) are listed below.

Illustrative compounds (IV):

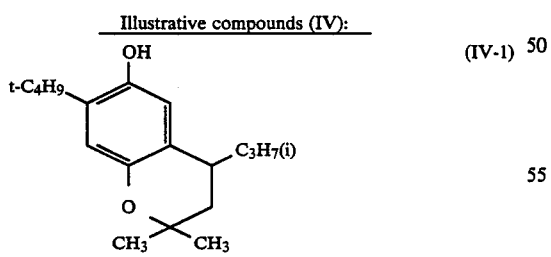
(IV-1)

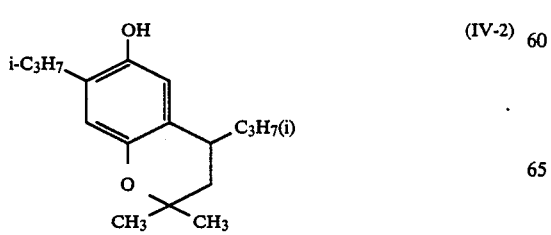
(IV-2)

-continued

Illustrative compounds (IV):

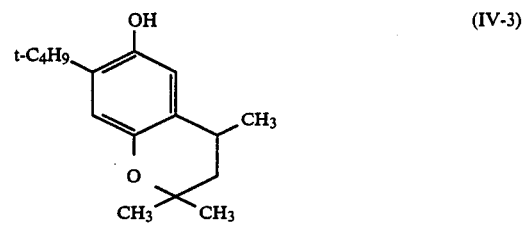
(IV-3)

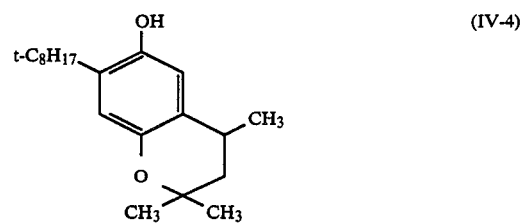
(IV-4)

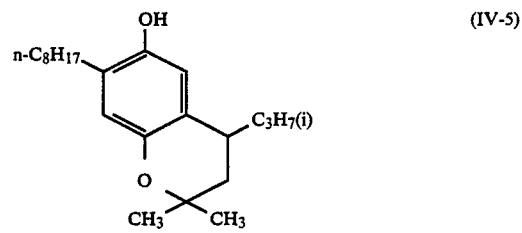
(IV-5)

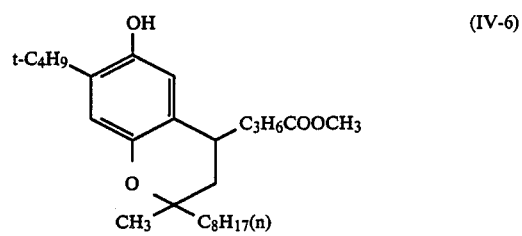
(IV-6)

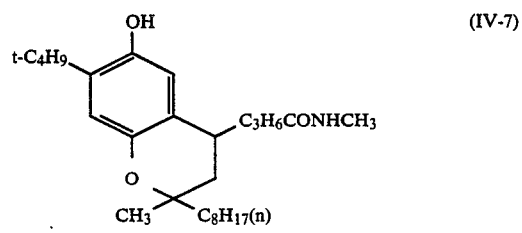
(IV-7)

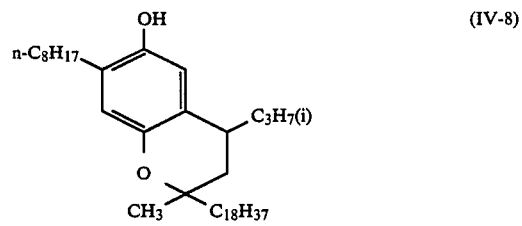
(IV-8)

-continued
Illustrative compounds (IV):
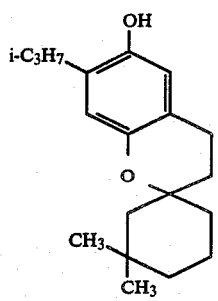 (IV-9)
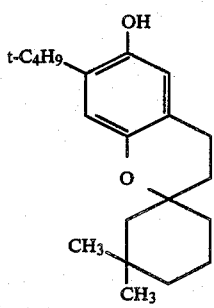 (IV-10)
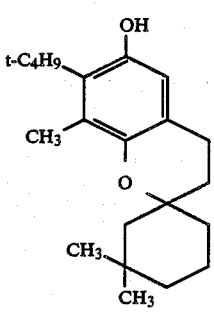 (IV-11)
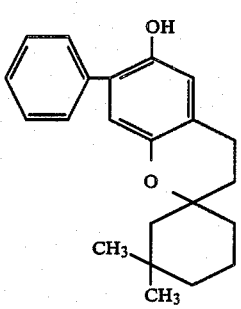 (IV-12)
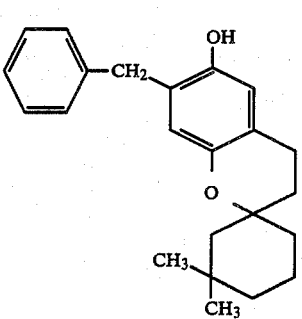 (IV-13)
-continued
Illustrative compounds (IV):
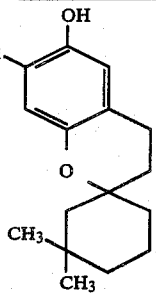 (IV-14)
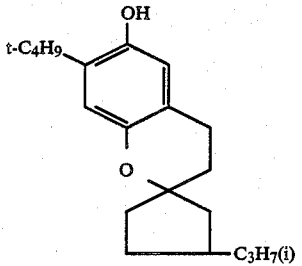 (IV-15)
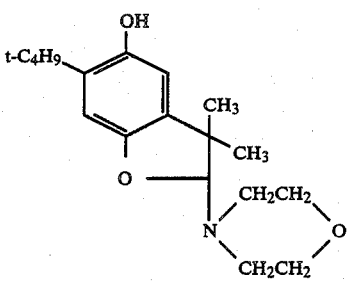 (IV-16)
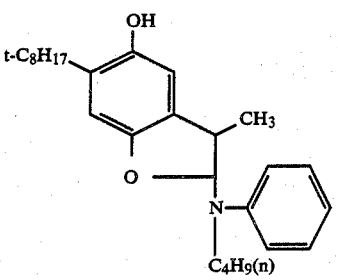 (IV-17)
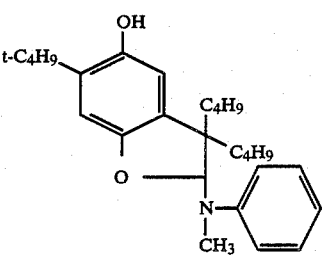 (IV-18)
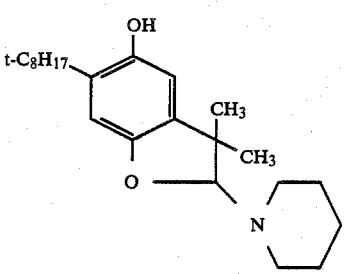 (IV-19)

-continued
Illustrative compounds (IV):
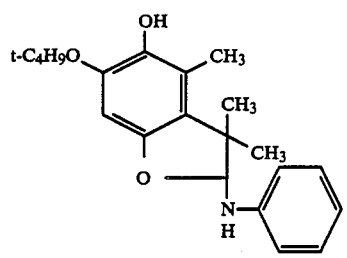 (IV-20)
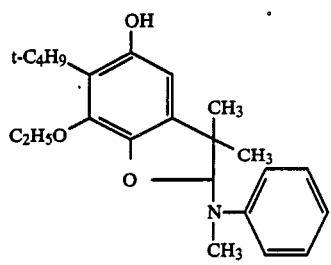 (IV-21)
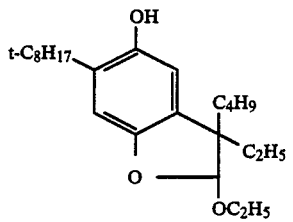 (IV-22)
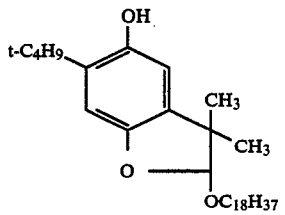 (IV-23)
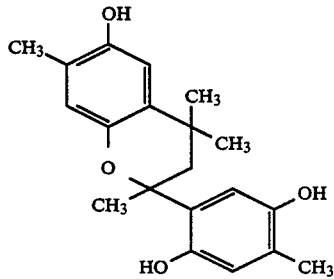 (IV-24)
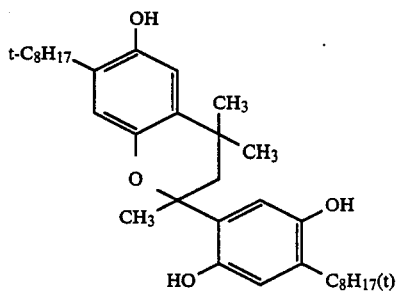 (IV-25)
-continued
Illustrative compounds (IV):
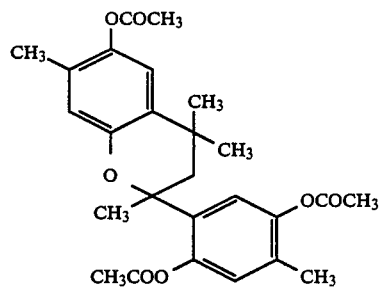 (IV-26)
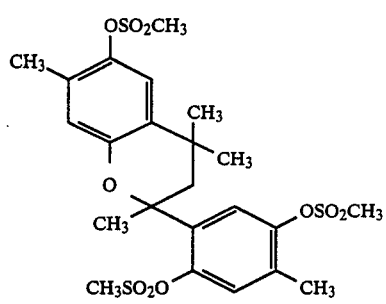 (IV-27)
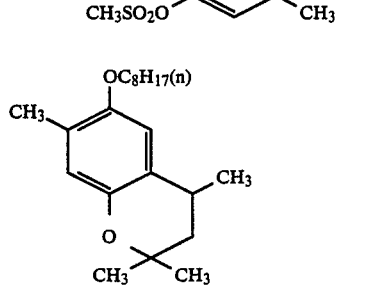 (IV-28)
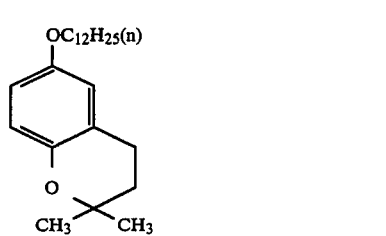 (IV-29)
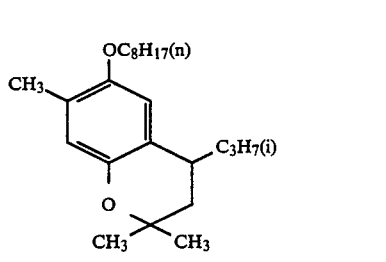 (IV-30)
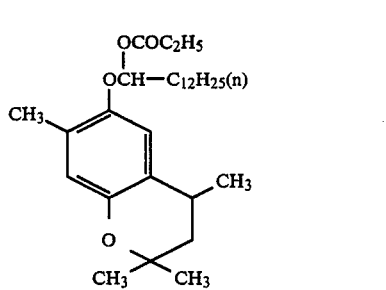 (IV-31)

-continued
Illustrative compounds (IV):

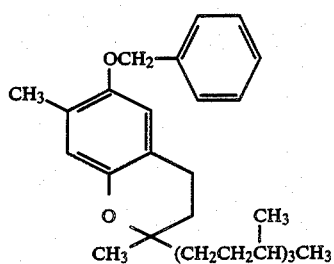
(IV-32)

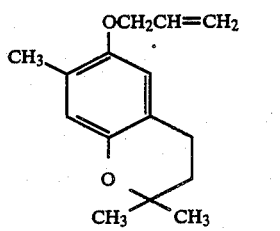
(IV-33)

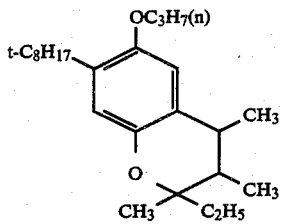
(IV-34)

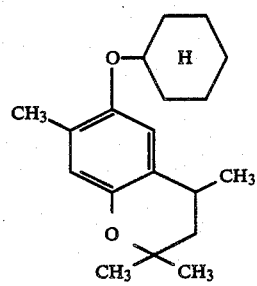
(IV-35)

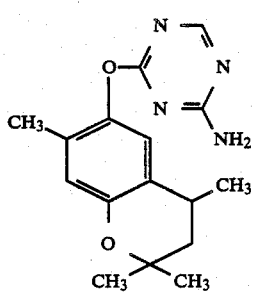
(IV-36)

-continued
Illustrative compounds (IV):

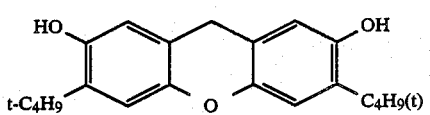
(IV-37)

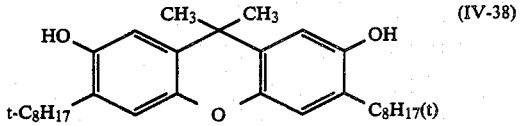
(IV-38)

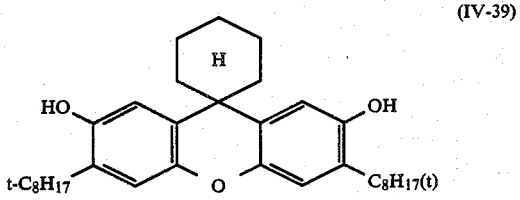
(IV-39)

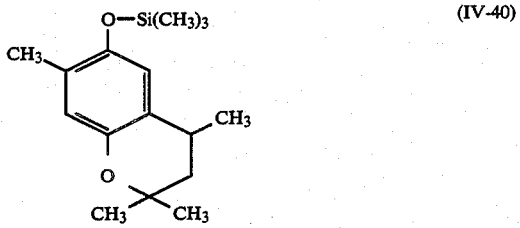
(IV-40)

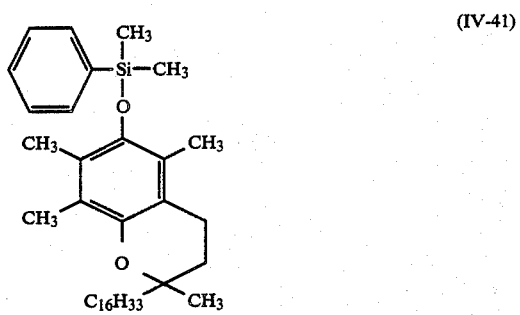
(IV-41)

The compounds formula (IV) listed above may be synthesized by any of the methods described in Japanese Patent Publication Nos. 14034/70, 8338/74, 6208/74, 21142/81, Unexamined Published Japanese Patent Application Nos. 77526/78, 147433/77, 39541/81, 77527/78 and 50244/80.

Illustrative examples of the compounds of formula (V) are listed below.

Illustrative Compounds (V):

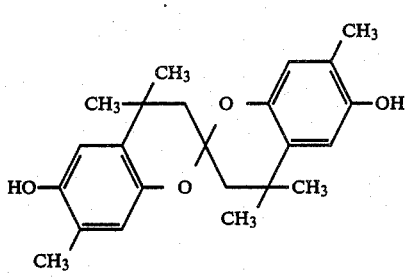
(V-1)

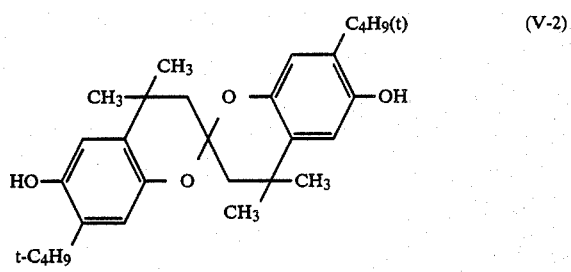
(V-2)

-continued
Illustrative Compounds (V):
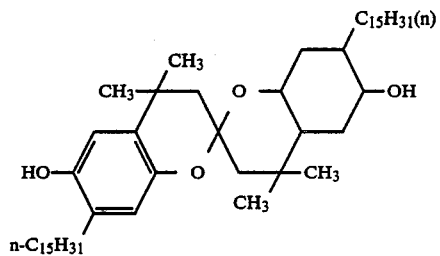 (V-3)
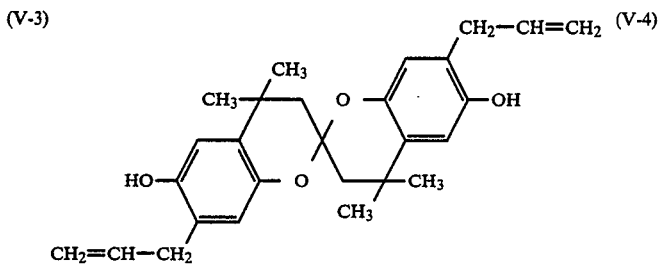 (V-4)
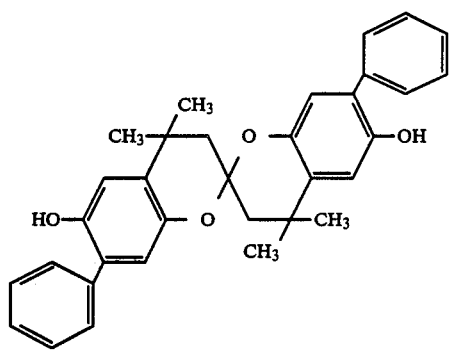 (V-5)
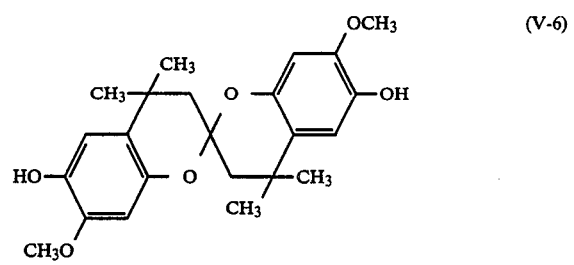 (V-6)
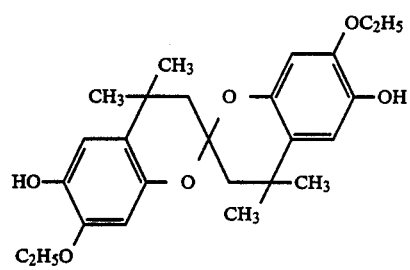 (V-7)
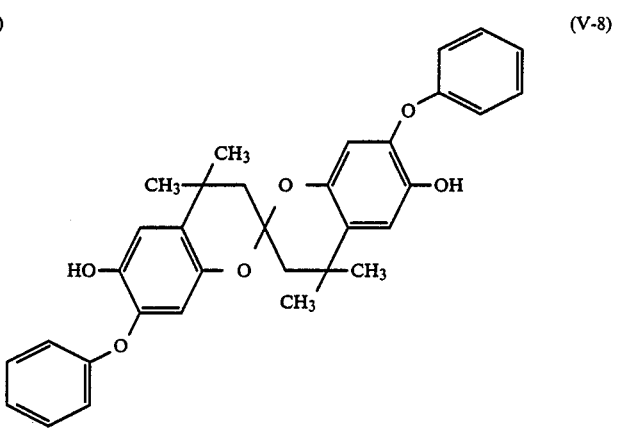 (V-8)
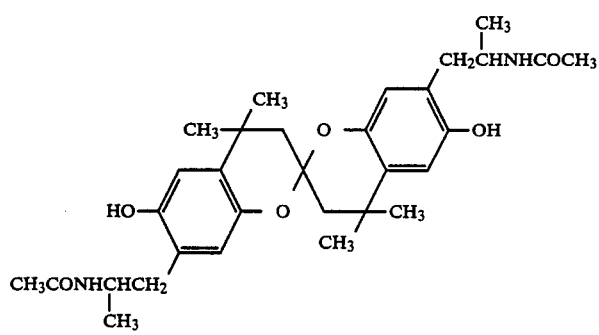 (V-9)

-continued
Illustrative Compounds (V):
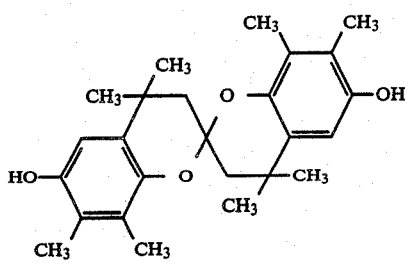
(V-10)
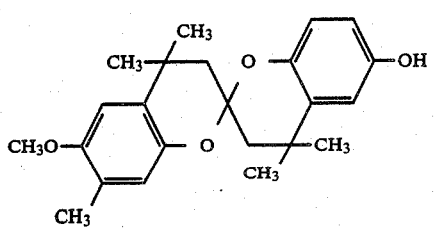
(V-11)
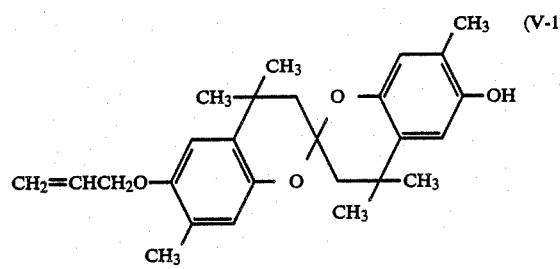
(V-12)
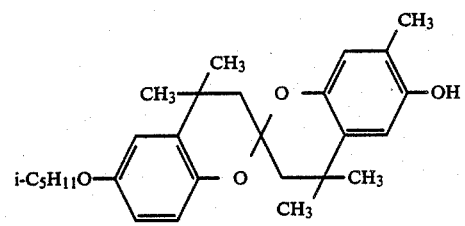
(V-13)
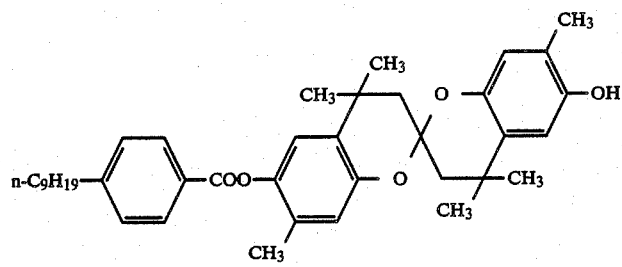
(V-14)
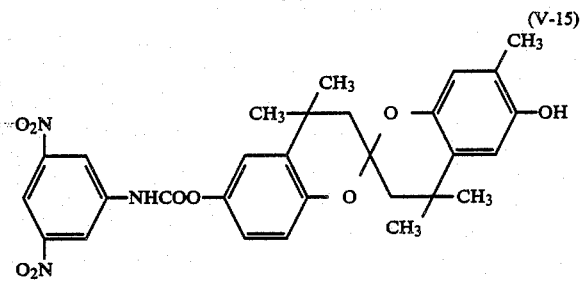
(V-15)
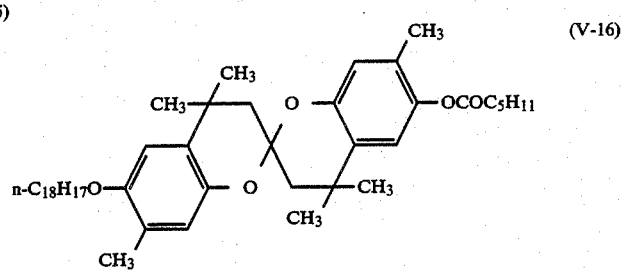
(V-16)
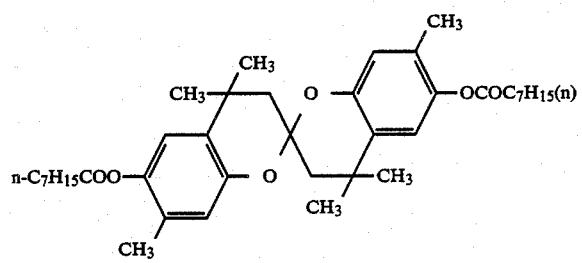
(V-17)
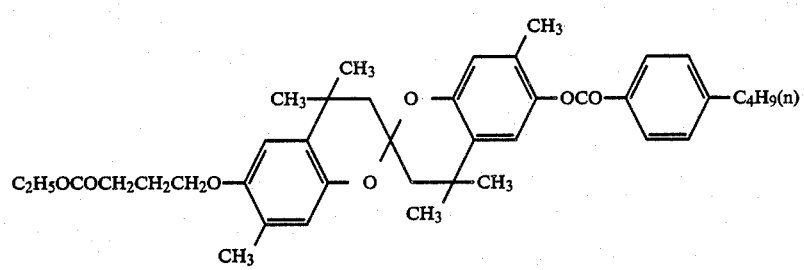
(V-18)

-continued
Illustrative Compounds (V):
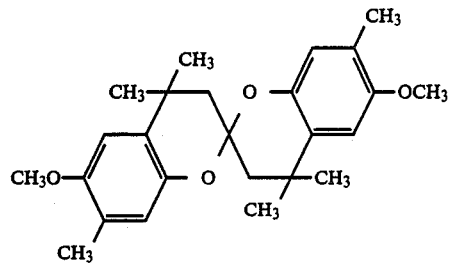 (V-19)
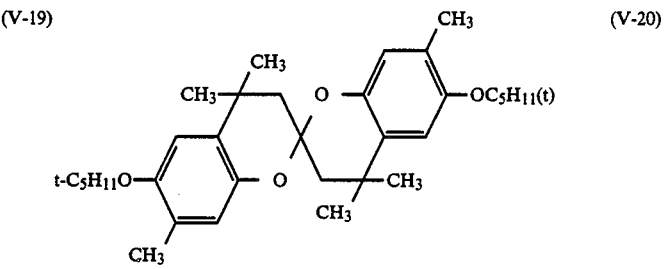 (V-20)
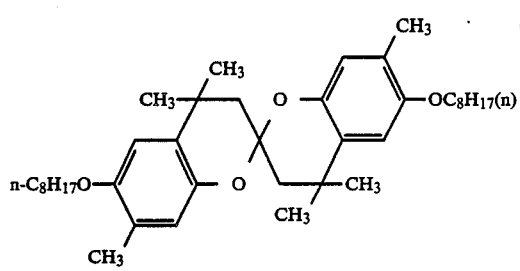 (V-21)
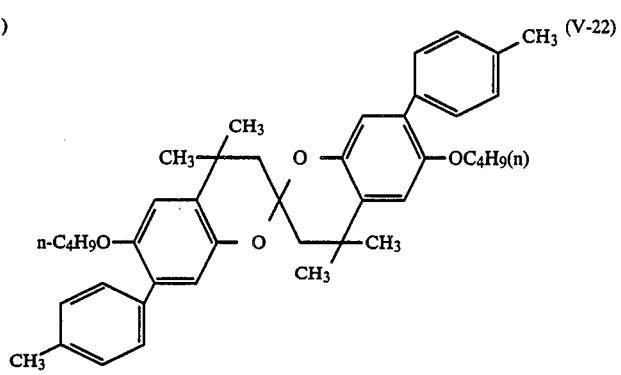 (V-22)
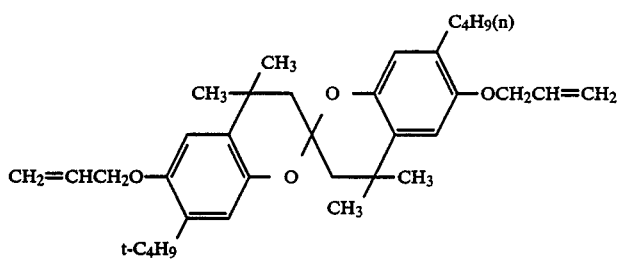 (V-23)
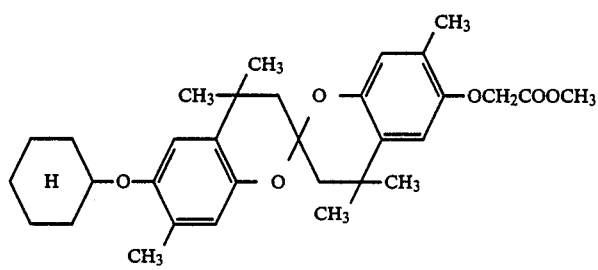 (V-24)
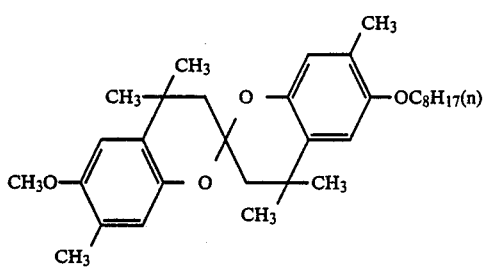 (V-25)

-continued
Illustrative Compounds (V):
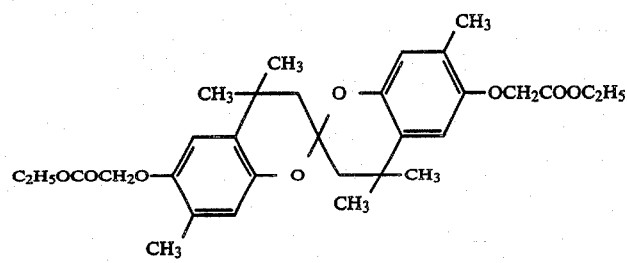
(V-26)
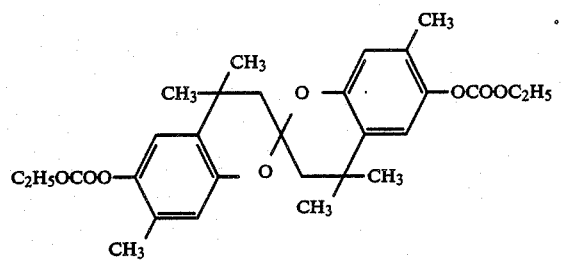
(V-27)
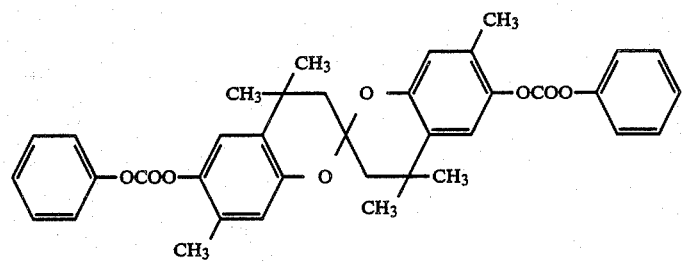
(V-28)
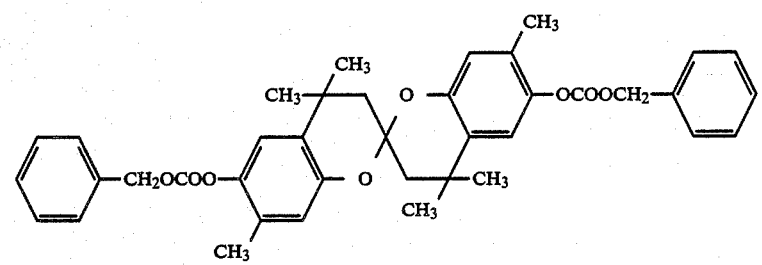
(V-29)
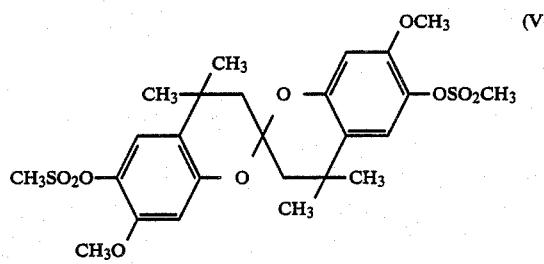
(V-30)
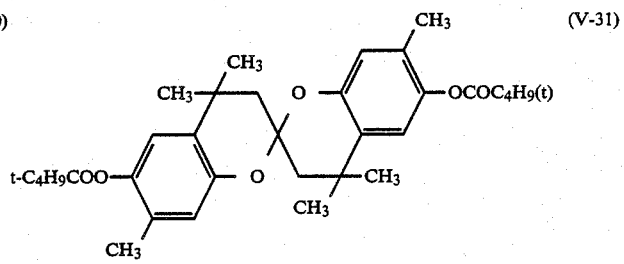
(V-31)
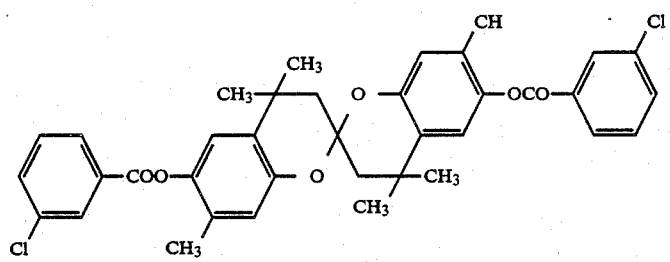
(V-32)

-continued
Illustrative Compounds (V):
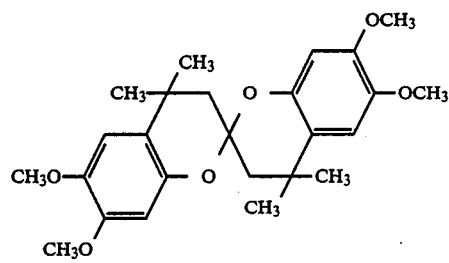
(V-33)
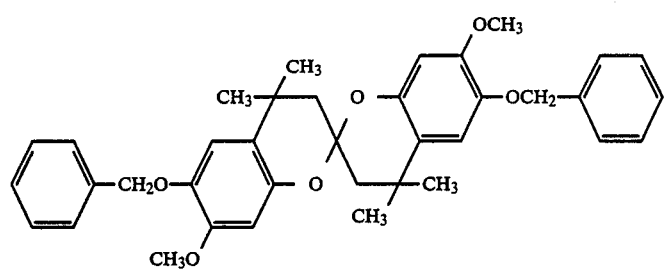
(V-34)
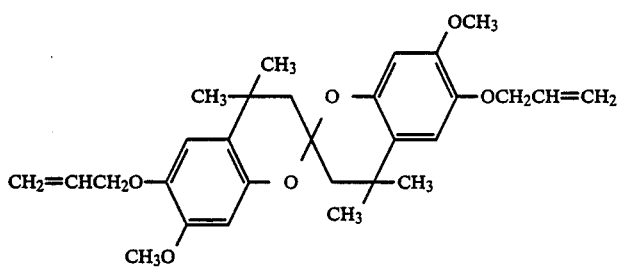
(V-35)
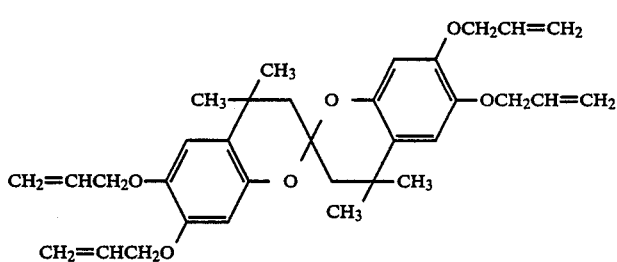
(V-36)
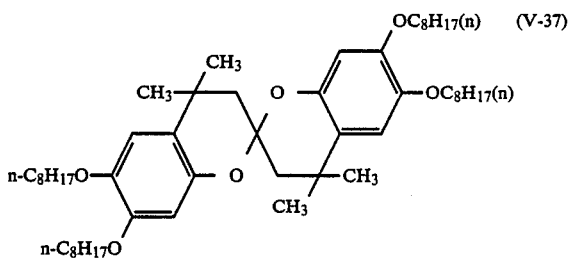
(V-37)
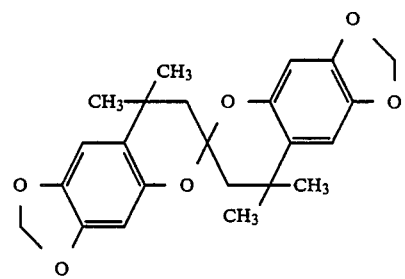
(V-38)

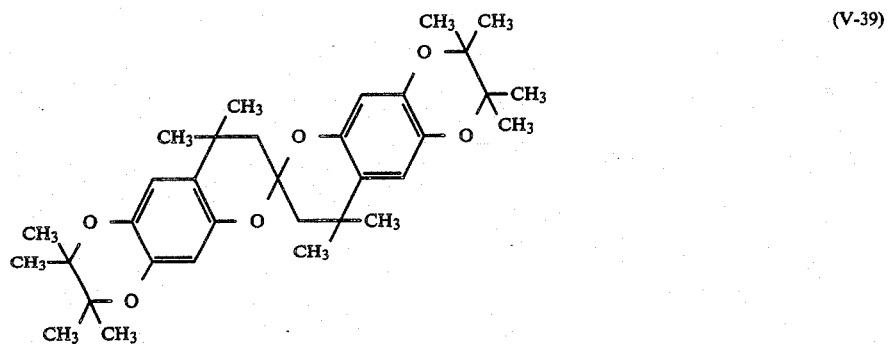
(V-39)
The compounds of formula (V) listed above may be synthesized by any of the methods described in Japanese Patent Publication Nos. 52747/81, 19763/82, 9765/82, Unexamined Published Japanese Patent Application Nos. 17729/78 and 70840/80.
Illustrative examples of the compounds of formula (VI) are listed below.
Illustrative compounds (VI)
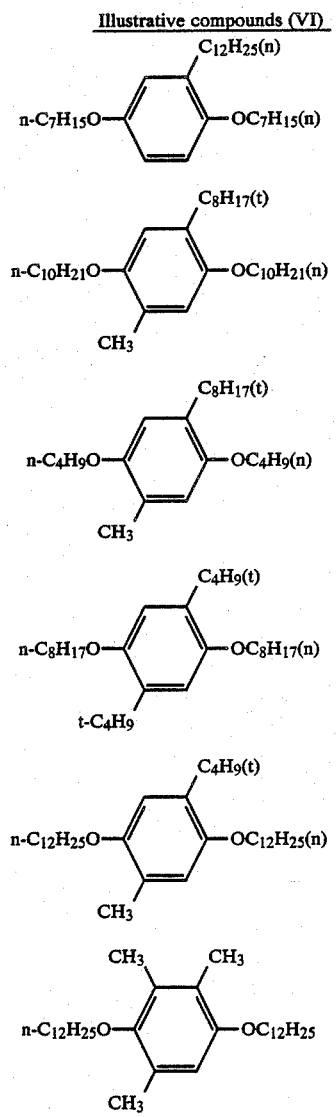
-continued
Illustrative compounds (VI)
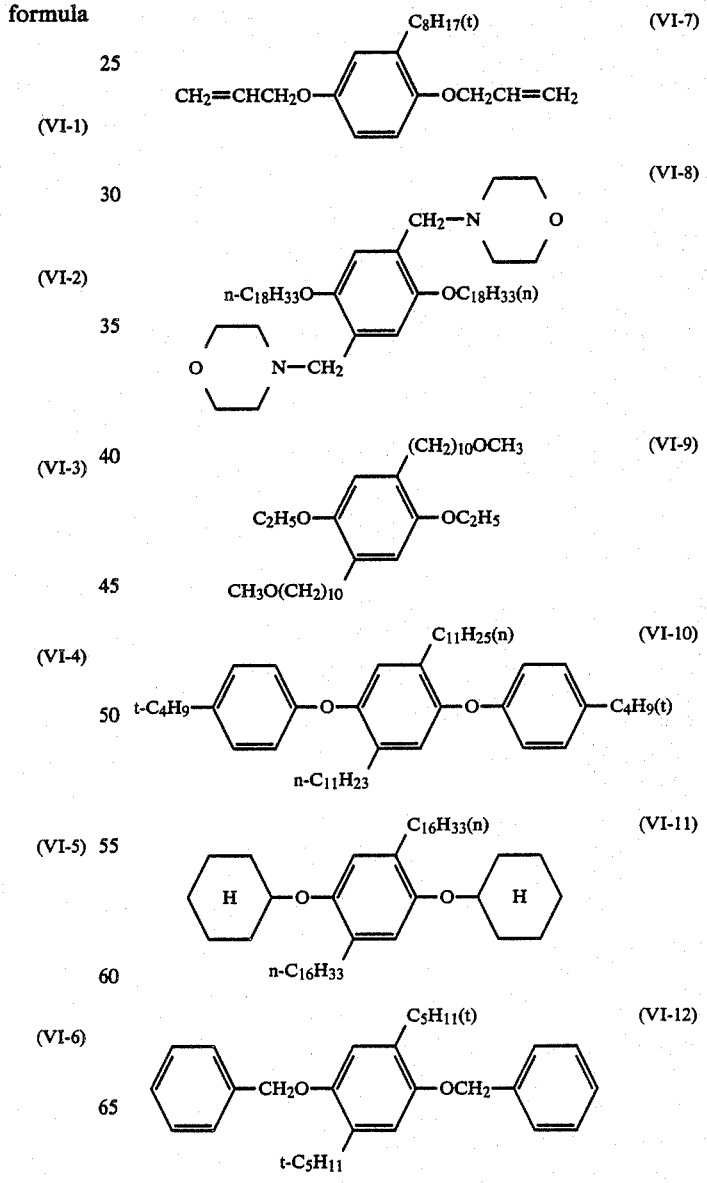

-continued
Illustrative compounds (VI)
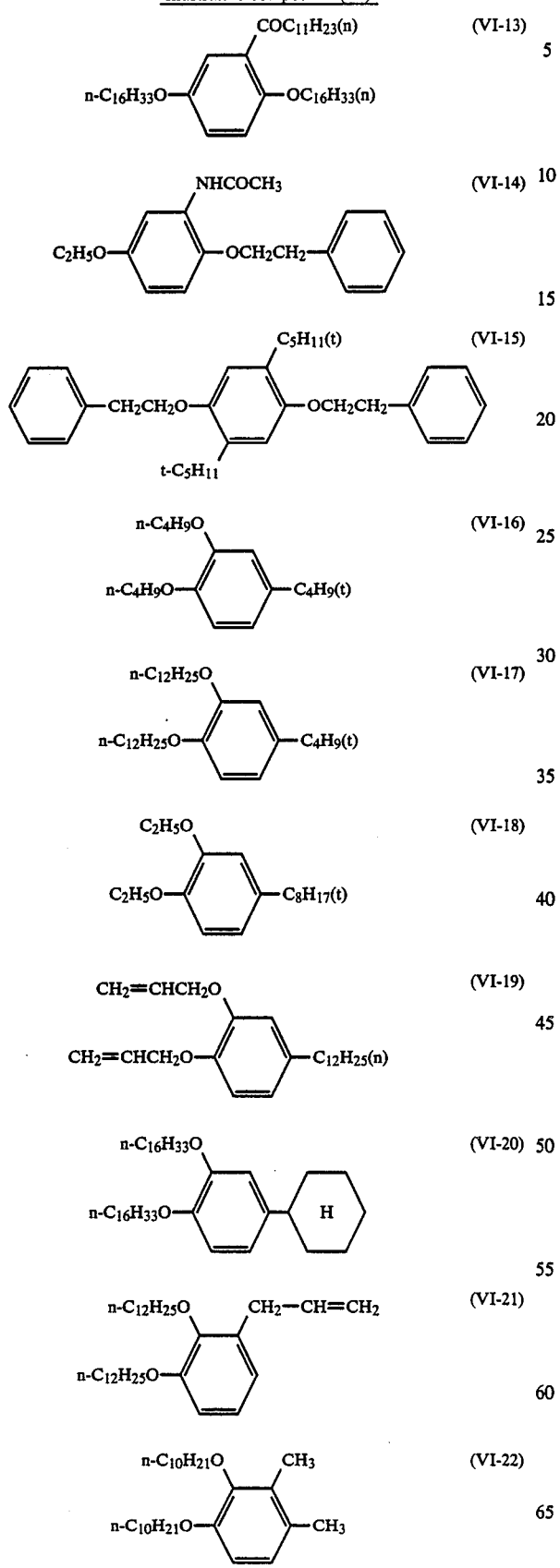
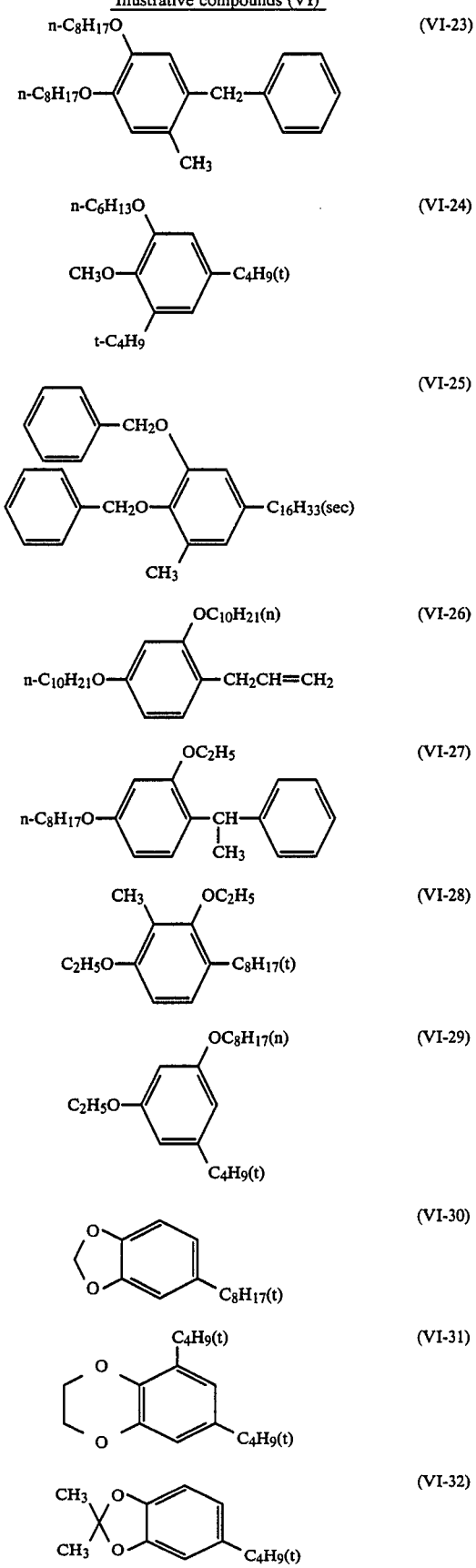

-continued
Illustrative compounds (VI)

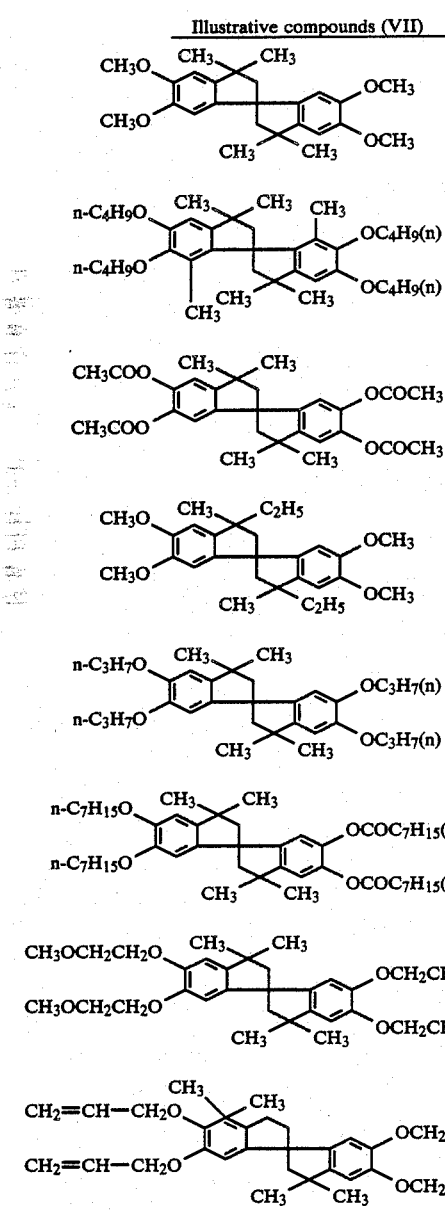

The compounds of formula (VI) listed above may be synthesized by any of the methods described in Japanese Patent Publication No. 24257/81, and Unexamined Published Japanese Patent Application Nos. 145530/79, 52747/81 and 39541/81.

Illustrative examples of the compounds of formula (VII) are listed below

-continued
Illustrative compounds (VII)

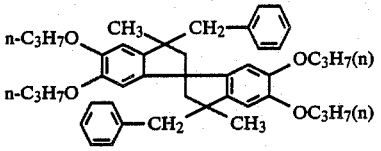

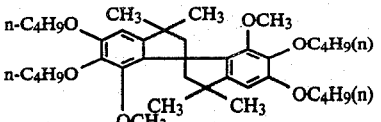

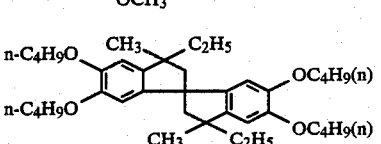

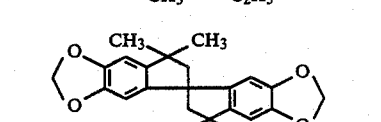

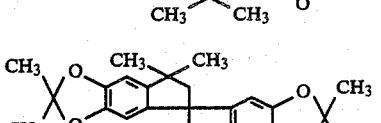

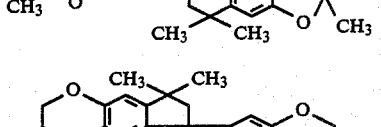

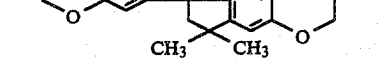

The compounds of formula (VII) listed above may be synthesized in accordance with the methods described in Unexamined Published Japanese Patent Application Nos. 52747/81 and 159644/81.

If the compound of formula (IV), (V), (VI) or (VII) is contained in a light-sensitive silver halide emulsion layer together with the ether compounds of the present invention, such compound is used in an amount ranging from 5 to 200 wt %, preferably from 10 to 100 wt %, of the coupler used. If the compound of formula (IV), (V), (VI) or (VII) is incorporated in a non-sensitive layer adjacent the light-sensitive silver halide emulsion layer, such compound is used in an amount ranging from 0.01 to 1 g, preferably from 0.02 to 0.5 g, per square meter of the color photographic material. If the ether compounds of the present invention are used together with the compound of formula (IV), (V), (VI) or (VII), the two compounds may be incorporated in the same layer or separate layers. The following five cases are possible: (1) the ether compounds of the present invention and the compound of formula (IV), (V), (VI) or (VII) are incorporated in the same light-sensitive silver halide emulsion layer; (2) the ether compounds of the present invention are incorporated in the light-sensitive silver halide emulsion layer whereas the anti-discoloration compound is incorporated in a non-sensitive layer adjacent said light-sensitive silver halide emulsion layer; (3) both the ether compounds of the present invention and anti-discoloration compound are incorporated in a layer adjacent the light-sensitive silver halide emulsion layer; (4) the ether compounds of the present invention are incorporated in a non-sensitive layer whereas the anti-discoloration compound is incorporated in the light-sensitive silver halide emulsion layer; and (5) the two compounds are incorporated in both the light-sensitive silver halide emulsion layer and a layer adjacent thereto.

When the ether compounds of the present invention are used in combination with the anti-discoloration compound, or compound of formula (IV), (V), (VI) or (VII), the ratio of the latter to the former is in the range of 0.05–10, preferably 0.1–5.

Known anti-discoloration agents may be used in combination with, or substituted for, the compound of formula (IV), (V), (VI) or (VII), in addition to the ether compounds of the present invention. Particularly preferred examples of the known anti-discoloration agents include bisphenols of the type described in Japanese Patent Publication Nos. 31256/73.and 31625/73; α-tocopherols and their acyl derivatives of the type described in U.S. Pat. No. 2,360,290 and Unexamined Published Japanese Patent Application No. 27333/76; organometallic chelate compounds of the type described in U.S. Pat. No. 4,050,938, Unexamined Published Japanese Patent Application Nos. 62826/79, 62987/79, 82385/79 and 82386/79; and hydroxybenzoic acid esters of the type described in Unexamined Published Japanese Patent Application No. 48535/79.

One or more of the known anti-discoloration agents listed above may be used in combination with the ether compounds of the present invention.

The advantages of the color photographic material in accordance with the present invention are exhibited to the fullest if a non-diffusible bisphenolic compound is also present in the above described silver halide emulsion layer containing a non-diffusible coupler. A suitable non-diffusible bisphenolic compound may be selected from among those described in Japanese Patent Publication Nos. 31256/73, 31625/73, 12055/79; Unexamined Published Japanese Patent Application Nos. 72225/77, 52421/78 and 154325/79. Preferred non-diffusible bisphenolic compounds are those which are represented by the following formula (VIII):

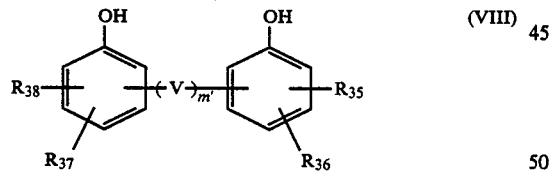

wherein $R_{35}$, $R_{36}$, $R_{37}$ and $R_{38}$ are each a hydrogen atom, an alkyl group or an alkenyl group, provided that at least one of $R_{35}$ and $R_{36}$ and at least one of $R_{37}$ and $R_{38}$ are each an alkyl group; V is —O—, —S— or an alkylene group; m' is 0 or 1.

Illustrative but non-limiting examples of the bisphenolic compounds of formula (VIII) are listed below.

Illustrative compounds (VIII):

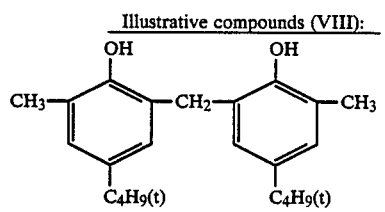

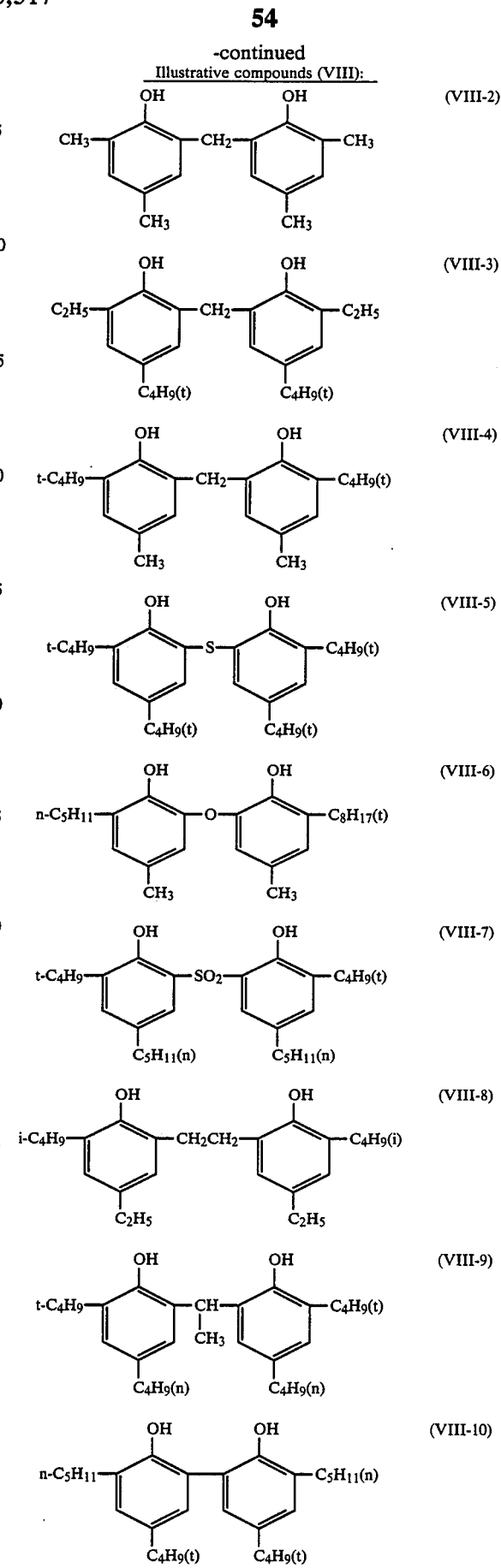

-continued
Illustrative compounds (VIII):

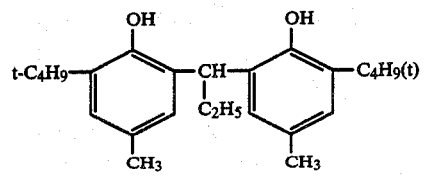 (VIII-11)

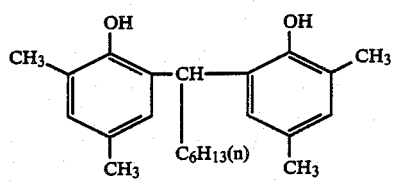 (VIII-12)

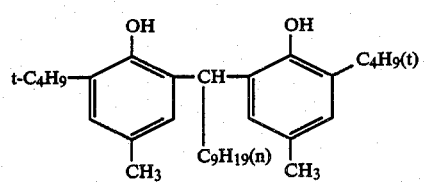 (VIII-13)

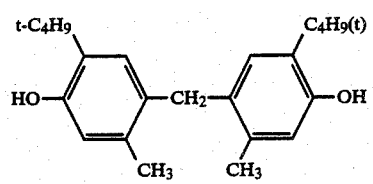 (VIII-14)

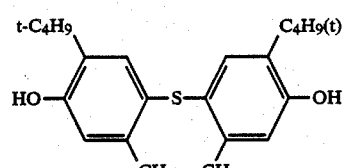 (VIII-15)

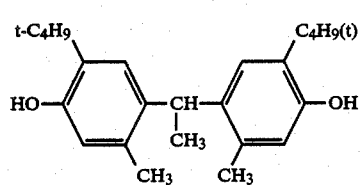 (VIII-16)

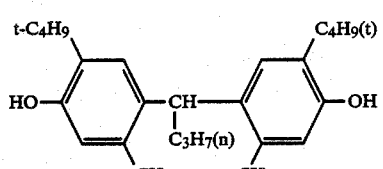 (VIII-17)

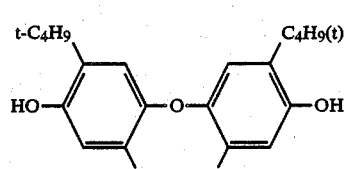 (VIII-18)

-continued
Illustrative compounds (VIII):

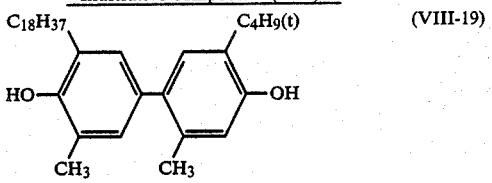 (VIII-19)

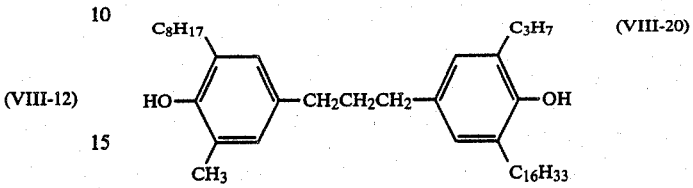 (VIII-20)

The silver halide incorporated in the silver halide emulsion layer in accordance with the present invention may be any type of silver halide such as silver iodobromide, silver chlorobromide, silver bromide, silver chloroiodobromide, silver chloride and silver chloroiodide.

These silver halides may be prepared by ammoniacal, neutral or acidic process. Also, they may be prepared by the double-jet precipitation, normal precipitation, or reverse single-jet method or the halide conversion method. The interior of the silver halide grains may have a distinct or diffuse borderline between different halide compositions, and either of these types of silver halide grains may be effectively used in the present invention.

Gelatin (alkali- or acid-treated) is most commonly used as a binder in the photographic layers, including light-sensitive and non-sensitive layers, making up the silver halide color photographic material of the present invention. Such gelatin may be used in combination with a gelatin derivative (e.g. phthalated gelatin or phenylcarbamoyl gelatin), albumin, agar, gum arabic, alginic acid, partially hydrolyzed cellulose derivative, partially hydrolyzed poly(vinyl acetate), polyacrylamide, poly(vinyl alcohol), polyvinylpyrrolidone, or copolymers of these vinyl compounds.

The silver halide emulsion used in the present invention may be chemically sensitized by a variety of techniques which include noble metal sensitization with noble metal (e.g. ruthenium, rhodium, palladium, iridium, platinum or gold) salts (e.g. ammonium chloropalladate, potassium chloroplatinate, potassium chloropalladite and potassium chloroaurate), sulfur sensitization with activated gelatin or instable sulfur compounds (e.g. sodium thiosulfate), selenium sensitization with a selenium compound, and reduction sensitization with a stannous salt, polyamine or under pAg condition.

Also, the silver halide emulsions may be optically sensitized with a variety of sensitizing dyes in order to impart sensitivity to the desired wavelengths in the spectrum. Preferred sensitizing dyes are cyanine dyes, merocyanine dyes and complex cyanine dyes of the types described in U.S. Pat. Nos. 1,939,201, 2,072,908, 2,739,149, 2,213,995, 2,493,748, 2,519,001; German Pat. No. 929,080; and British Pat. No. 505,979. These sensitizing dyes may be used either alone or in combination. Such sensitizing dyes may be used for purposes other than sensitization, such as fog prevention, avoiding the timedependent deterioration of the photographic performance of the silver halide color photographic material, and regulation of development (e.g. tone control).

The color photographic material in accordance with the present invention may also contain chemical sensitizers and stabilizers to an extent that is not detrimental to the objects of the invention. Illustrative chemical sensitizers are thioether compounds, quaternary ammonium salt compounds and polyalkylene oxide compounds, and exemplary stabilizers are triazoles, imidazoles, azaindenes, benzothiazolium compounds, zinc compounds, cadmium compounds and mercaptans.

The color photographic material of the present invention may further contain a variety of photographic additives such as UV absorbers (e.g. benzophenone compounds and benzotriazole compounds), development accelerators (e.g. 1-aryl-3-pyrazolidone compounds), surfactants (e.g. sodium alkylnaphthalenesulfonate, sodium alkylbenzenesulfonate, sodium alkylsulfosuccinate, and polyalkylene compounds), water-soluble anti-irradiation dyes (e.g. azo compounds, styryl compounds, oxonol compounds, anthraquinone compounds and triphenylmethane compounds), hardeners (e.g. halogen-substituted S-triazine compounds, active vinyl compounds, ethyleneimino compounds, epoxy compounds and water-soluble aluminum salts), and agents to improve the properties of photographic coats (e.g. glycerin, polyalkylene glycols, aqueous polymer dispersions (e.g. latexes), and solid or liquid paraffins.

Various supports may be used for preparing the color photographic material of the present invention, and they include single supports made of such materials as paper, glass, cellulose acetate, cellulose nitrate, polyester, polyamide and polystyrene, as well as laminations of such materials, for example, the lamination of paper and polyolefin (e.g. polyethylene or polypropylene). Suitable supports may be selected depending upon the need. The supports may be subjected to a variety of surface treatments in order to provide a better adhesion to silver halide emulsions. For example, the surface of the support may be grained by either mechanical treatment or treatment with an organic solvent. Alternatively, electron bombardment or flame treatment techniques may be used, or the provision of a subbing layer may be effected.

Individual layers making up the color photographic material of the present invention may be applied to a suitable support by any of the known coating techniques such as dip coating, roller coating, bead coating, and curtain-flow coating. The web is subsequently dried.

The basic steps for processing the color photographic material of the present invention comprise color development, bleaching and fixing. The respective steps may be independent or more than one step may be accomplished by a single treatment using a processing solution capable of performing the necessary functions. For example, a bleach-fixing solution may be used to perform bleaching and fixing at the same time. Each of the color developing, bleaching and fixing steps may be effected in two or more stages. One possible method of processing consists of color development, first fixing and bleach-fixing. The process may further include the steps of prehardening, neutralization, first development (black-and-white development), image stabilization and washing.

Several of the processing schemes that may be desirably used to process the color photographic material of the present invention are listed below. The respective steps in each scheme are performed in a continuous fashion.

(1) Color development→bleach-fixing →washing;
(2) Color development→bleaching→washing→fixing-→washing;
(3) Color developing→stopping→bleaching→washing-→fixing→washing;
(4) Black-and-white development→reversal exposure→color development→bleach-fixing→washing; and
(5) black-and-white development→stopping→color development in the presence of a foggant→bleaching→washing→fixing→washing.

The color photographic material of the present invention is processed at temperatures that are properly determined depending upon the type of the material to be processed and the processing scheme. Generally, temperatures in the range of 20°-60° C. are used, and the color photographic material of the present invention is particularly adapted to processing at temperatures not lower than 30° C.

The color developing agents used in the color developer may include any of the known compounds extensively used in various color photographic processes. Particularly useful color developing agents are N,N-dialkyl-p-phenylenediamines, wherein the alkyl and phenyl groups may or may not be substituted. Especially useful compounds are listed below: N,N-diethyl-p-phenylenediamine hydrochloride, N-methyl-p-phenylenediamine hydrochloride, N,N-dimethyl-p-phenylenediamine hydrochloride, 2-amino-5-(N-ethyl-N-dodecylamino)-toluene, N-ethyl-N-$\beta$-methanesulfonamidoethyl-3-methyl-4-aminoaniline sulfate, N-ethyl-N-$\beta$-hydroxylethylaminoaniline sulfate, 4-amino-3-methyl-N,N-diethylaniline hydrochloride, N-ethyl-N-$\beta$-hydroxyethyl-3-methyl-4-aminoaniline sulfate, and 4-amino-N-($\beta$-methoxyethyl)-N-ethyl-3-methylaniline-p-toluene sulfonate.

Particularly good results are obtained with the color photographic material of the present invention if the color developing agent used is N-ethyl-N-$\beta$-sulfonamidoethyl-3-methyl-4-aminoaniline sulfate or 4-amino-N-($\beta$-methoxyethyl)-N-ethyl-3-methylaniline-p-toluene sulfonate. These color developing agents may be incorporated in the color photographic material as they are or in the form of their precursors. Precursors for color developing agents are those compounds which are capable of producing color developing agents under alkaline conditions, and may include Schiff base type precursors obtained by reaction with aromatic aldehyde derivatives, precursors of polyvalent metallic ion complexes, precursors of phthalimide derivatives, precursors of phosphamide derivatives, precursors of sugar amine reaction products, and urethane type precursors. These precursors for aromatic primary amine color developing agents are described in, for example, U.S. Pat. Nos. 3,342,599, 2,507,114, 2,695,234, 3,719,492; British Pat. No. 803,783; Unexamined Published Japanese Patent Application Nos. 135628/78, 79035/79; and Research Disclosure Nos. 15,159, 12,146 and 13,924. If the color developing agent or a precursor therefor is incorporated in a color photographic material, any known alkaline processing solution (which is generally referred to as an activator bath) may be used as a color developer to process that photographic material.

The aromatic primary amine color developing agents or precursors therefor must be incorporated in sufficient amounts to produce practically acceptable levels of color as a result of color development. The necessary amounts will differ greatly depending upon the type of the color photographic material to be processed but generally, they range from 0.1 to 5 moles, preferably from 0.5 to 3 moles, per mol of the light-sensitive silver halide. The color developing agents or precursors therefor shown above may be used either alone or in combination with themselves. Such compounds may be incorporated in the color photographic material of the present invention in various methods; for example, they may be incorporated in the form of a solution in a suitable solvent such as water, methanol, ethanol or acetone, or they may be incorporated in the form of a dispersion using a high-boiling organic solvent such as dibutyl phthalate, dioctyl phthalate or tricresyl phosphate. Alternatively, they may be incorporated after being impregnated in a latex polymer, as shown in Research Disclosure No. 14,850.

In addition to the aromatic primary amine compound used as the color developing agent, the color developer in accordance with the present invention may optionally contain other additives such as an alkali agent (e.g. sodium hydroxide, potassium hydroxide, potassium carbonate or trisodium phosphate), a pH buffer (e.g. boric acid or acetic acid), a known development accelerator (e.g. thioethers, 1-aryl-3-pyrazolidones, N-methyl-p-aminophenols, or polyalkylene glycol), an organic solvent (e.g. benzyl alcohol, ethanol, butanol, ethylene glycol, diethylene glycol, acetone or N,N-dimethylformamide), a development restrainer (potassium bromide or nitrobenzimidazole), a preservative (e.g. sulfite, hydroxylamine, glucose, alkanol or amines), and a water softener (e.g. polyphosphoric acid compound or nitrilotriacetic acid).

The color developer used in the present invention generally has a pH of 7.0 or higher, preferably between about 9.5 and 13.0.

The color development in accordance with the present invention is preferably performed at between 30° and 40° C. for a period of 2 to 5 minutes.

If, in accordance with the processing scheme of the present invention, bleaching and fixing are effected separately, the former generally precedes the latter. If a bleach-fixing solution is used, the two steps are carried out in a single bath containing that blix solution. Illustrative examples of the bleaching agents that can be used in the bleaching solution or blix solution include potassium ferricyanide, bichromic acid salt, iron salt of aminopolycarboxylic acid, metal salt of aliphatic polycarboxylic acid and persulfate salt. For the purposes of the present invention, metal complex salts of organic acids are preferably used. The particular advantages that result from using metal complex salts of organic acids in the processing solution are that they effectively prevent the problems of precipitation and reduced bleaching ability.

The metal complex salts of organic acids in accordance with the present invention have the ability to oxidize the metallic silver that is produced by development and convert it to silver halide. The structure of the metal complex salts is such that a metal (e.g. iron, cobalt or copper) is coordinated with an organic acid such as aminopolycarboxylic acid, oxalic acid or citric acid. The organic acids most preferred for use in forming such metal complex salts are the aminopolycarboxylic acids represented by the following formulas (IX) and (X):

HOCO—A$_1$—Z—A$_2$—COOH   (IX)

-continued

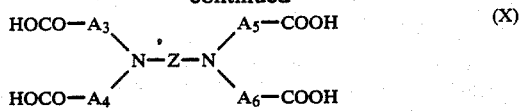   (X)

wherein A$_1$, A$_2$, A$_3$, A$_4$, A$_5$ and A$_6$ are each a divalent hydrocarbon group such as an alkylene group, a cycloalkylene group or an arylene group; Z is a divalent hydrocarbon group such as alkylene, cycloalkylene or arylene, or —O—, —S— or

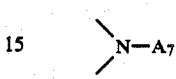

(wherein A$_7$ is a monovalent hydrocarbon group such as alkyl, cycloalkyl or aryl, or a lower aliphatic carboxylic acid group).

These aminopolycarboxylic acids may be in the form of their alkali metal salts, ammonium salts or water-soluble amine salts. Typical examples of the aminopolycarboxylic acids of formulas (IX) and (X) are listed below:
ethylenediaminetetraacetic acid;
diethylenetriaminepentaacetic acid;
ethylenediamine-N-(β-hydroxyethyl)-N,N′,N′-triacetic acid;
propylenediaminetetraacetic acid;
nitrilotriacetic acid;
cyclohexanediaminetetraacetic acid;
iminodiacetic acid;
methyliminodiacetic acid;
ethyliminodiacetic acid;
hydroxyethyliminodiacetic acid;
hydroxylmethyliminodiacetic acid;
propyliminodiacetic acid;
butyliminodiacetic acid;
dihydroxyethylglycine;
ethyletherdiaminetetraacetic acid;
glycoletherdiaminetetraacetic acid;
ethylenediaminetetrapropionic acid;
phenylenediaminetetraacetic acid;
ethylenediaminetetraacetic acid disodium salt;
ethylenediaminetetraacetic acid tetra(trimethylammonium) salt;
ethylenediaminetetraacetic acid tetrasodium salt;
diethylenetriaminepentaacetic acid pentasodium salt;
ethylenediamine-N-(β-hydroxyethyl)-N,N′, N′triacetic acid sodium salt;
propylenediaminetetraacetic acid sodium salt;
nitrilotriacetic acid sodium salt; and
cyclohexanediaminetetraacetic acid sodium salt.

Metals in the metal complex salts of organic acids in accordance with the present invention are those which are capable of coordinating with the organic acids listed above and examples are chromium, manganese, iron, coblat, nickel and copper. Particularly preferred metal complex salts of organic acids in accordance with the present invention are those of the higher valency metals, such as ferric salts.

While all combinations of the organic acids and metals listed above may be used as the metal complex salts of organic acids, particularly preferred are the ferric salts of ethylenediaminetetraacetic acid, such as ethylenediaminetetraacetic acid iron (III) sodium salt and ethylenediaminetetraacetic acid iron (III) ammonium salt. Two or more metal complex salts of organic acids having different structures may be used together. The preferred range of the amount of the metal complex salt of organic acid is from 0.01 to 0.4 mole per liter of the processing solution.

The bleaching solution used in the present invention may contain various additives in addition to the bleaching agent (i.e., metal complex salt of organic acid). A desirable additive is a re-halogenating agent such as an alkali halide or ammonium halide (e.g. potassium bromide, sodium bromide, sodium chloride or ammonium bromide). Other suitable additives include a pH buffer (e.g. borate, oxalate, acetate, carbonate or phosphate salt), a solubilizer (e.g. triethanolamine) and any other additives that are commonly incorporated in the bleaching solution, such as aminopolycarboxylic acid or salts thereof, alkylamines or polyethylene oxides.

A bleach-fixing solution may be used in the present invention which basically consists of the bleaching agent which is a metal complex salt (e.g. iron salt) of an organic acid, in combination with a silver halide fixing agent such as thiosulfate, thiocyanate or thiourea. In addition to the bleaching agent and the silver halide fixing agent, a small or an increased amount of a halogen compound such as potassium bromide may also be used. A special blix solution may be used which is composed of the bleaching agent and a large amount of a halogen compound such as potassium bromide.

Potassium bromide is not the only example of a halogen compound that can be used in the bleach-fixing solution and other usable compounds are hydrochloric acid, hydrobromic acid, lithium bromide, sodium bromide, ammonium bromide, potassium iodide and ammonium iodide.

The silver halide fixing agent incorporated in the bleach-fixing solution may be selected from among those compounds of the type commonly used in the ordinary fixing treatment which react with silver halide to form a water-soluble complex salt; typical examples are thiosulfates such as potassium thiosulfate, sodium thiosulfate and ammonium thiosulfate; thiocyanates such as potassium thiocyanate, sodium thiocyanate and ammonium thiocyanate; thiourea, thioether, highly concentrated bromides and iodides.

The bleach-fixing solution may also contain a pH buffer selected from among boric acid, acetic acid, and a variety of salts such as borax, sodium hydroxide, potassium hydroxide, sodium carbonate, potassium carbonate, sodium bicarbonate, potassium bicarbonate, sodium acetate and ammonium hydroxide. Such pH buffers may be used either alone or in combination with themselves. The bleach-fixing solution may further contain a variety of brighteners, anti-foaming agents or surfactants.

If desired, the bleach-fixing solution may contain a preservative (e.g. hydroxylamine, hydrazine, sulfite, metabisulfite, or a bisulfite adduct of aldehyde or ketone compound), an organic chelating agent (e.g. aminopolycarboxylic acid), a solubilizer (e.g. alkanolamine), an anti-stain agent (e.g. organic amine), or an organic solvent (e.g. methanol, N,N-dimethylformamide, or N,N-dimethylsulfoxide).

If an autoprocessor is used in the processing of the color photographic material of the present invention, the bleaching solution or bleach-fixing solution is usually supplied with a replenisher by an automatic replenishing system. The replenisher has the following three functions: compensation of the components in the bleaching solution or bleach-fixing solution that are consumed as the photographic material is processed; compensation for the dilution by the carryover from the color developer or rinsing water; and compensation of the components that are carried out of the bleaching solution or bleach-fixing solution by the photographic material being processed. In order to perform these functions, the replenisher is usually more concentrated than the bleaching solution or bleach-fixing solution and the degree of such concentration is properly selected depending upon the amounts of the components to be compensated or the amount of the bleaching solution or bleach-fixing solution.

The duration of the bleaching or blixing step in accordance with the present invention is generally in the range of 0.5–2 minutes, preferably 1–1.5 minutes. The processing temperature is generally in the range of 25°–40° C.

The washing step in the processing scheme in accordance with the present invention is generally carried out for a period of 1–4 minutes using water at 25°–35° C. The amount of rinsing water used depends on the type of silver halide color photographic material to be processed and is generally in the range of 0.5–50 liters per square meter of the photographic material.

The following examples are provided for further illustrations of the advantages of the present invention and should not be construed as limiting. Unless otherwise noted, the amounts of all components used in the Examples are those per square meter of the photographic material.

EXAMPLE 1

A polyethylene-coated paper support was provided with the following three layers. Five samples of color photographic material were prepared by using different ether compounds in accordance with the present invention. Layer 1 (immediately adjacent the substrate): containing 2.1 g of gelatin, 0.35 g (as silver) of a green-sensitive silver chlorobromide emulsion (68 mol % silver bromide, average grain size=0.45 μm), and 0.3 g of dioctyl phthalate (DOP) having dissolved therein $0.58 \times 10^{-3}$ mole of magenta coupler M-8, 0.015 g of 2,5-di-t-octylhydroquinone (HQ-1) and one of the ether compounds indicated in Table 1. Layer 2: containing 1.4 g of gelatin and 0.4 g of DOP having dissolved therein 0.4 g of UV absorber (UV-1) and an equal amount of UV-2.

Layer 3: a gelatin protective layer containing 1.3 g of gelatin and 0.04 g of 2,4-dichloro-6-hydroxy-S-triazine sodium salt (hardener).

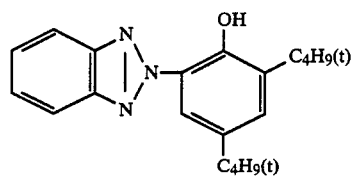

UV-1

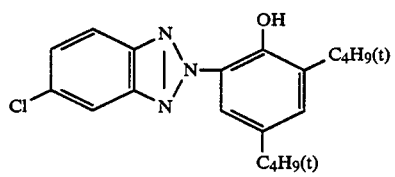

UV-2

The five samples of color photographic material thus prepared were exposed through an optical wedge and subsequently processed by the following scheme.

| Steps | Temperature °C. | Time |
|---|---|---|
| Color development | 33 | 1 min 30 sec |
| Bleach-fixing | 33 | 1 min |
| Washing | 30–34 | 1 min |
| Drying | 60–80 | 1 min |

The color developer and the bleach-fixing solution used had the following formulations.

| Components | Amounts |
|---|---|
| Color developer | |
| Pure water | 800 ml |
| Ethylene glycol | 15 ml |
| Benzyl alcohol | 15 ml |
| Hydroxylamine sulfate | 2 g |
| Potassium carbonate | 32 g |
| Potassium bromide | 0.65 g |
| Sodium chloride | 1.0 g |
| Potassium sulfite | 2.0 g |
| N—Ethyl-N—β-methanesulfonamido-ethyl-3-methyl-4-aminoaniline sulfate | 4.5 g |
| Whitex BB (50% aq. sol.) | 2 ml |
| (brightener of Sumitomo Chemical Co., Ltd.) | |
| 1-Hydroxyethylidene-1,1-diphosphonic acid (60% aq. sol.) | 2 ml |
| Pure water to make | 1,000 ml |
| pH adjusted to 10.1 with 10% potassium hydroxide or dilute sulfuric acid. | |
| Bleach-fixing solution | |
| Pure water | 550 ml |
| Color developer A | 200 ml |
| Ethylenediaminetetraacetic acid iron (III) ammonium salt | 65 g |
| Ammonium thiosulfate | 85 g |
| Sodium bisulfite | 10 g |
| Sodium metabisulfite | 2 g |
| Ethylenediaminetetraacetic acid disodium salt | 12 g |
| Sodium bromide | 10 g |
| Potassium chloride | 1.0 g |
| Pure water to make | 1,000 ml |
| pH adjusted to 7.0 with dilute sulfuric acid or conc. ammonia water. | |

Each of the processed samples was divided into four portions and tested for their resistance to light, heat and moisture by the following procedures.

Light resistance: The sample was exposed to light for 400 hrs. in a xenon weather meter (Model WEL-6X-HC of Suga Test Instruments Co., Ltd.).

Heat resistance: The sample was held in a constant-temperature chamber (70° C.) for 3 weeks.

Moisture resistance: The sample was held in a humidistat (70° C., 80% r.h.) for 2 weeks.

The reflection densities on the background of each sample were measured with a densitometer (Model Macbeth TR-924) using three monochromatic lights, B (blue), G (green) and R (red). The results are shown in Table 1. The numerals in the columns of "Light Resistance", "Heat Resistance" and "Moisture Resistance" were obtained by subtracting the reflection density at the background of a fresh sample from the reflection density at the background of a specific test sample.

TABLE 1

| Sample No. | | Ether compound | Light resistance | | | Heat resistance | | | Moisture resistance | | |
|---|---|---|---|---|---|---|---|---|---|---|---|
| | | | B | G | R | B | G | R | B | G | R |
| 1 | Comparative sample | — | 0.29 | 0.06 | 0.01 | 0.16 | 0.12 | 0.03 | 0.46 | 0.20 | 0.04 |
| 2 | Sample of the present invention | 0.15 g (14) | 0.13 | 0.01 | 0.01 | 0.05 | 0.03 | 0.01 | 0.16 | 0.08 | 0.02 |
| 3 | Sample of the present invention | 0.15 g (19) | 0.11 | 0.01 | 0.00 | 0.04 | 0.03 | 0.02 | 0.19 | 0.05 | 0.02 |
| 4 | Sample of the present invention | 0.15 g (29) | 0.06 | 0.01 | 0.00 | 0.03 | 0.02 | 0.01 | 0.11 | 0.04 | 0.02 |
| 5 | Sample of the present invention | 0.15 g (30) | 0.08 | 0.02 | 0.00 | 0.03 | 0.02 | 0.01 | 0.13 | 0.05 | 0.02 |

The results in Table 1 show that sample Nos. 2 to 5 incorporating the alkenyl ether compounds of the present invention had less staining, particularly smaller yellow staining, in the background than comparative sample No. 1 when they were exposed to light, heat and moisture.

EXAMPLE 2

Samples of color photographic material were prepared and tested as in Example 1 except that magenta coupler M-4 was used in combination with one or more of the known anti-discoloration agents indicated in Table 2. The results of the tests conducted for evaluating the resistance of the samples to light, heat and moisture are also shown in Table 2.

TABLE 2

| Sample No. | | Ether compound | Anti-discoloration agent | | Light resistance | | | Heat resistance | | | Moisture resistance | | |
|---|---|---|---|---|---|---|---|---|---|---|---|---|---|
| | | | | | B | G | R | B | G | R | B | G | R |
| 6 | Comparative sample | — | — | | 0.27 | 0.06 | 0.01 | 0.15 | 0.12 | 0.03 | 0.45 | 0.19 | 0.04 |
| 7 | " | — | ST-1 | 0.1 g | 0.25 | 0.05 | 0.01 | 0.15 | 0.11 | 0.03 | 0.46 | 0.20 | 0.05 |
| 8 | " | — | ST-1 VI-12 | 0.1 g 0.2 g | 0.26 | 0.06 | 0.02 | 0.16 | 0.10 | 0.03 | 0.44 | 0.19 | 0.04 |
| 9 | " | — | VII-5 | 0.2 g | 0.29 | 0.07 | 0.02 | 0.16 | 0.11 | 0.03 | 0.45 | 0.20 | 0.04 |
| 10 | Sample of the present invention | (19) | — | | 0.13 | 0.02 | 0.00 | 0.07 | 0.02 | 0.02 | 0.20 | 0.05 | 0.02 |
| 11 | Sample of the present invention | " | ST-1 VI-12 | 0.1 g 0.2 g | 0.09 | 0.01 | 0.01 | 0.05 | 0.02 | 0.02 | 0.16 | 0.03 | 0.01 |
| 12 | Sample of the present invention | " | VII-5 | 0.2 g | 0.09 | 0.01 | 0.01 | 0.04 | 0.01 | 0.01 | 0.14 | 0.02 | 0.01 |
| 13 | Sample of the present invention | (29) | — | | 0.09 | 0.01 | 0.00 | 0.03 | 0.02 | 0.00 | 0.09 | 0.04 | 0.01 |

TABLE 2-continued

| Sample No. | Ether compound | Anti-discoloration agent | | Light resistance | | | Heat resistance | | | Moisture resistance | | |
|---|---|---|---|---|---|---|---|---|---|---|---|---|
| | | | | B | G | R | B | G | R | B | G | R |
| 14 | Sample of the present invention | " | ST-1 0.1 g VI-12 0.2 g | 0.04 | 0.01 | 0.00 | 0.03 | 0.01 | 0.00 | 0.09 | 0.04 | 0.01 |
| 15 | Sample of the present invention | " | VII-5 0.2 g | 0.04 | 0.01 | 0.00 | 0.02 | 0.01 | 0.00 | 0.09 | 0.05 | 0.01 |
| 16 | Sample of the present invention | (33) | V-21 0.2 g | 0.09 | 0.01 | 0.01 | 0.04 | 0.01 | 0.01 | 0.07 | 0.03 | 0.01 |
| 17 | Sample of the present invention | " | — | 0.15 | 0.01 | 0.01 | 0.05 | 0.02 | 0.01 | 0.17 | 0.04 | 0.01 |
| 18 | Sample of the present invention | " | IV-1 0.2 g | 0.11 | 0.01 | 0.01 | 0.05 | 0.02 | 0.01 | 0.10 | 0.03 | 0.01 |

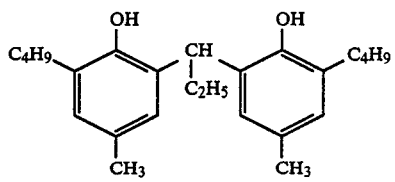

ST-1

As will be clear from Table 2, sample Nos. 10–18 prepared in accordance with the present invention exhibited good properties and had less stain in the background. The effectiveness against light stain of the ether compounds in accordance with the present invention was enhanced by incorporating known anti-discoloration agents.

EXAMPLE 3

A paper support coated with polyethylene on both sides was surface-treated by corona discharge and provided with the following seven layers. Six samples of multi-layer color photographic paper were prepared by using different ether compounds.

Layer 1: containing 1.5 g of gelatin, 0.33 g (as silver) of a blue-sensitive silver chlorobromide emulsion (85 mol % silver bromide, average grain size=0.65 μm) and 0.25 g of DOP having dissolved therein $0.6 \times 10^{-3}$ mole of yellow coupler (Y-1), $0.9 \times 10^{-3}$ mole of Y-2 and 0.015 g of HQ-1.

Layer 2: containing 1.0 g of gelatin and 0.06 g of DOP having 0.09 g of HQ-1 dissolved therein.

Layer 3: containing 1.3 g of gelatin, 0.27 g (as silver) of a green-sensitive silver chlorobromide emulsion (50 mol % silver bromide, average grain size=0.45 μm), 0.2 g of DOP having dissolved therein $0.59 \times 10^{-3}$ mole of magenta coupler M-8, 0.015 g of HQ-1 and 0.1 g of anti-discoloration agent (compound IV-12), and 0.15 g of AID-1 (anti-irradiation dye).

Layer 4: containing 1.5 g of gelatin, and 0.6 g of DOP having dissolved therein 0.8 g of UV-1 and 0.04 g of HQ-1.

Layer 5: containing 1.3 g of gelatin, 0.3 g (as silver) of a red-sensitive silver chlorobromide emulsion (50 mol % silver bromide, average grain size=0.35 μm) and 0.2 g of DOP having dissolved therein $0.25 \times 10^{-3}$ mole of cyan coupler (C-1), $0.5 \times 10^{-3}$ mole of C-2, and 0.005 g of HQ-1.

Layer 6: containing 1.0 g of gelatin, and 0.015 g of DOP having dissolved therein 0.4 g of UV-2 and 0.01 g of HQ-1.

Layer 7: containing 1.0 g of gelatin, 0.015 g of polyvinylpyrrolidone and 0.015 g of filter dye AID-2.

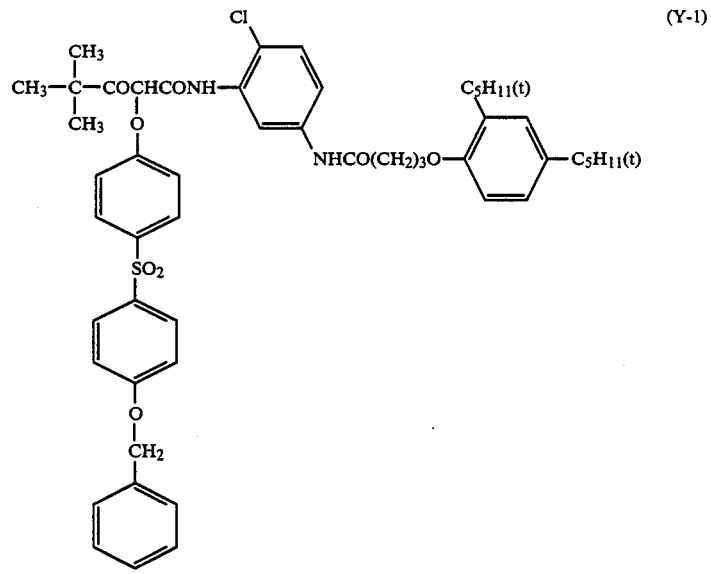

(Y-1)

-continued

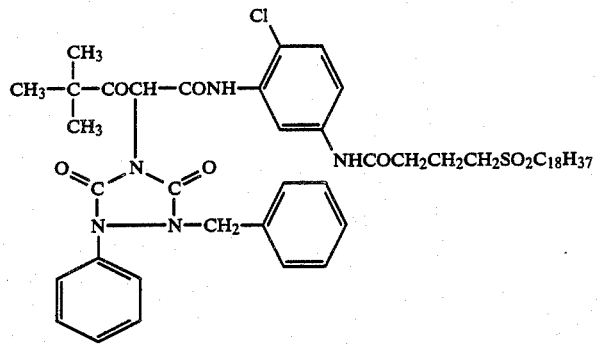 (Y-2)

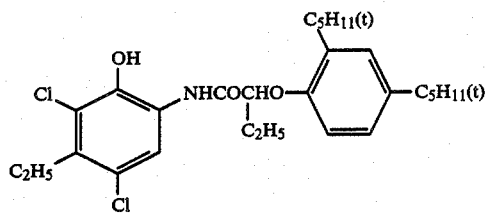 (C-1)

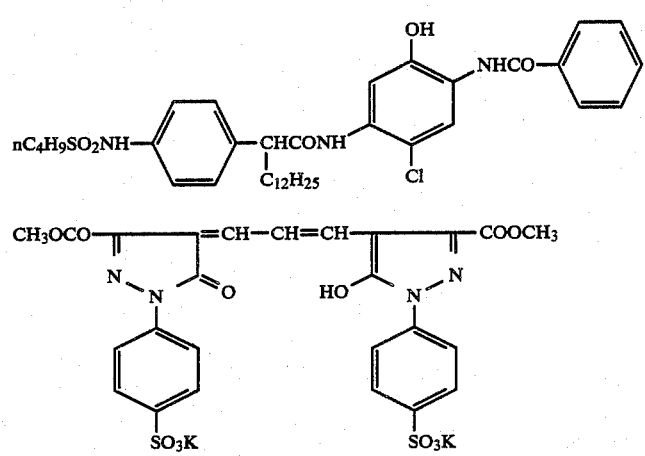 (C-2)

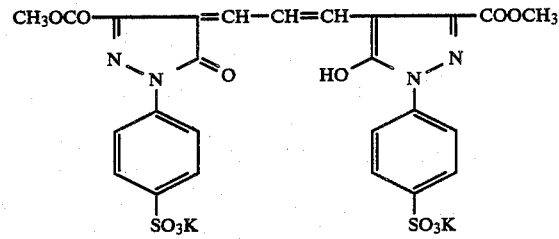 (AID-1)

The third layer containing magenta coupler M-8 also contained 0.15 g of one of the compounds indicated in Table 3.

Each of the samples contained 2,4-dichloro-6-hydroxy-s-triazine sodium salt (as hardener) in layers 2, 4 and 7 in the following amounts:

| | |
|---|---|
| Layer 2 | 0.03 g |
| Layer 4 | 0.03 g |
| Layer 7 | 0.04 g |

The six samples of multi-layer color photographic paper were left to stand at 30° C. for 4 days. Thereafter, the samples were exposed through an optical wedge to a monochromatic green light and subsequently processed by the following scheme:

| Steps | Temperature °C. | Time |
|---|---|---|
| Color development | 33 | 2 min 30 sec |
| Bleach-fixing | 33 | 1 min |
| Washing | 30–34 | 2 min |
| Drying | 70 ± 10 | 2 min |

The formulations of the color developer and the bleach-fixing solution were the same as those used in Example 1.

The processed samples were tested for the image keeping quality as in Example 1. The results are shown in Table 3.

TABLE 3

| Sample No. | | Ether compound | Light resistance | | | | Heat resistance | | | | Moisture resistance | | | |
|---|---|---|---|---|---|---|---|---|---|---|---|---|---|---|
| | | | B | G | R | G discoloration percent | B | G | R | G discoloration percent | B | G | R | G discoloration percent |
| 19 | Comparative sample | — | 0.34 | 0.10 | 0.03 | −45% | 0.20 | 0.14 | 0.05 | −5% | 0.51 | 0.22 | 0.05 | −10% |
| 20 | Comparative sample | Comparative compound E-4 0.15 g | 0.34 | 0.10 | 0.03 | −52% | 0.20 | 0.12 | 0.04 | −5% | 0.50 | 0.23 | 0.04 | −15% |

TABLE 3-continued

| Sample No. | | Ether compound | Light resistance | | | | Heat resistance | | | | Moisture resistance | | | |
|---|---|---|---|---|---|---|---|---|---|---|---|---|---|---|
| | | | B | G | R | G discoloration percent | B | G | R | G discoloration percent | B | G | R | G discoloration percent |
| 21 | Sample of the present invention | (19) 0.15 g | 0.18 | 0.05 | 0.02 | −40% | 0.08 | 0.04 | 0.02 | −4% | 0.21 | 0.10 | 0.03 | −4% |
| 22 | Sample of the present invention | (29) 0.15 g | 0.14 | 0.04 | 0.02 | −38% | 0.09 | 0.04 | 0.02 | −4% | 0.22 | 0.09 | 0.03 | −3% |

Comparative compound E-4:
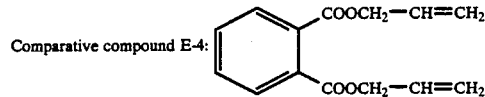

G discoloration percent: Discoloration of magenta dye image relative to the initial density which is 1.0.

The data in Table 3 show that the color photographic papers prepared in accordance with the present invention were sufficiently protected from staining in the background without causing any increased discoloration in the magenta dye image.

EXAMPLE 4

A polyethylene-coated paper support was provided with the following three layers. Twenty-four samples (Nos. 23–46) of color photographic material were prepared by using different anti-discoloration agents and ether compounds.

Layer 1: containing 2.1 g of gelatin, 0.36 g (as silver) of a green-sensitive silver chlorobromide emulsion (80 mol % silver bromide, average grain size=0.40 μm), and 0.4 g of DOP having dissolved therein $0.72 \times 10^{-3}$ mole of a magenta coupler (M-4), 0.018 g of HQ-1, and the anti-discoloration agents of formulas (IV)–(VII) or the ether compounds of formulas (Ia) and (Ib) shown in Table 4.

Layer 2: containing 1.6 g of gelatin, and 0.4 g of DOP having 0.5 g of UV-1 and 0.3 g of UV-2 dissolved therein.

Layer 3: a gelatin protective layer containing 1.3 g of gelatin and 0.05 g of 2,4-dichloro-6-hydroxy-S-triazine sodium salt.

In preparing layer 1, the magenta coupler, HQ-1, DOP and the anti-discoloration agent or the ether compound in accordance with the present invention were dissolved in four times the weight of the magenta coupler of ethyl acetate, and the resulting solution was mixed and dispersed in a 5% solution of sodium triisopropylnaphthalene sulfonate containing 1.5 times the weight of the magenta coupler of gelatin.

The twenty-four samples thus prepared were stored at 40° C. and 60% r.h. for 2 days. Thereafter, they were exposed through an optical wedge and subsequently processed by the following scheme.

| Steps | Temperature °C. | Time |
|---|---|---|
| Color development | 33 | 3 min 30 sec |
| Bleach-fixing | 33 | 1 min 30 sec |
| Washing | 30–34 | 3 min |
| Drying | 60–80 | 2 min |

The formulations of the color developer and bleach-fixing solution were the same as used in Example 1.

Each of the processed samples was divided into two portions. One group of the samples were exposed to light for 700 hours in a xenon weather meater (Model WEL-6X-HC of Suga Test Instruments Co., Ltd.) and the other group were left to stand in a humidistat (60° C.×50% r.h.) for 4 weeks. The reflection densities of the samples were measured using a green monochromatic light, and the percent discoloration for each sample was determined by the following formula, assuming the initial density as 1.0:

Percent discoloration=(1.0−density after discoloration)×100.

The blue density at the background (fogged area) of each sample was measured and Y-stain (change from the initial density) was determined. The results are shown in Table 4.

Sample Nos. 32 to 46 incorporating the anti-discoloration agent of formula (IV), (V), (VI) or (VII) in combination with the ether compound of formula (Ia) or (Ib) had lower percent light discolorations than sample Nos. 23 to 31. Additionally, sample Nos. 32 to 46 were comparable to sample Nos. 23 to 31 in terms of Y-stain and dark discoloration.

TABLE 4

| Sample No. | Anti-discoloration agent | | Ether compound | | Light discoloration | | Dark discoloration | |
|---|---|---|---|---|---|---|---|---|
| | Compound | Amount (g) | Compound | Amount (g) | Discoloration percent | Y-stain | Discoloration percent | Y-stain |
| 23 | — | — | — | — | 90 | 0.04 | 12 | 0.14 |
| 24 | — | — | 40 | 0.25 | 88 | 0.06 | 10 | 0.12 |
| 25 | — | — | 45 | 0.25 | 90 | 0.06 | 10 | 0.12 |
| 26 | — | — | 4 | 0.30 | 87 | 0.05 | 12 | 0.10 |
| 27 | IV-5 | 0.15 | — | — | 60 | 0.07 | 13 | 0.14 |
| 28 | IV-37 | 0.15 | — | — | 65 | 0.06 | 12 | 0.15 |
| 29 | V-7 | 0.15 | — | — | 62 | 0.07 | 10 | 0.15 |
| 30 | VI-4 | 0.15 | — | — | 58 | 0.06 | 12 | 0.15 |
| 31 | VII-6 | 0.15 | — | — | 63 | 0.07 | 12 | 0.16 |
| 32 | IV-5 | 0.15 | 40 | 0.25 | 40 | 0.05 | 10 | 0.11 |
| 33 | IV-5 | 0.15 | 45 | 0.25 | 38 | 0.04 | 9 | 0.10 |
| 34 | IV-5 | 0.15 | 4 | 0.3 | 35 | 0.05 | 10 | 0.10 |

TABLE 4-continued

| Sample No. | Anti-discoloration agent Compound | Amount (g) | Ether compound Compound | Amount (g) | Light discoloration Discoloration percent | Y-stain | Dark discoloration Discoloration percent | Y-stain |
|---|---|---|---|---|---|---|---|---|
| 35 | IV-37 | 0.15 | 40 | 0.25 | 45 | 0.04 | 10 | 0.10 |
| 36 | IV-37 | 0.15 | 45 | 0.25 | 40 | 0.04 | 9 | 0.09 |
| 37 | IV-37 | 0.15 | 4 | 0.3 | 37 | 0.04 | 10 | 0.11 |
| 38 | V-7 | 0.15 | 40 | 0.25 | 28 | 0.05 | 11 | 0.12 |
| 39 | V-7 | 0.15 | 45 | 0.25 | 25 | 0.06 | 12 | 0.10 |
| 40 | V-7 | 0.15 | 4 | 0.3 | 29 | 0.04 | 12 | 0.11 |
| 41 | VI-4 | 0.15 | 40 | 0.25 | 25 | 0.06 | 10 | 0.12 |
| 42 | VI-4 | 0.15 | 45 | 0.25 | 21 | 0.04 | 10 | 0.11 |
| 43 | VI-4 | 0.15 | 4 | 0.3 | 26 | 0.04 | 8 | 0.09 |
| 44 | VII-6 | 0.15 | 40 | 0.25 | 36 | 0.06 | 10 | 0.10 |
| 45 | VII-6 | 0.15 | 45 | 0.25 | 30 | 0.05 | 11 | 0.10 |
| 46 | VII-6 | 0.15 | 4 | 0.3 | 33 | 0.04 | 11 | 0.11 |

EXAMPLE 5

Sixteen samples of color photographic material were prepared as in Example 4 except that anti-discoloration agent (VII-10) and/or ether compound (47) was incorporated in the emulsion dispersion in layer 1. The magenta couplers used are indicated in Table 5. Sample Nos. 47–62 were processed and tested as in Example 4, and the results are shown in Table 5, from which one can see that the effectiveness of the present invention in inhibiting light discoloration was exhibited with the four magenta couplers used.

TABLE 5

| Sample No. | Magenta coupler | Anti-discoloration agent VII-10 (g) | Ether compound (47) (g) | Light discoloration Discoloration percent | Y-stain | Dark discoloration Discoloration percent | Y-stain |
|---|---|---|---|---|---|---|---|
| 47 | M-4 | — | — | 87 | 0.04 | 11 | 0.14 |
| 48 | " | — | 0.3 | 88 | 0.05 | 10 | 0.13 |
| 49 | " | 0.2 | — | 53 | 0.05 | 10 | 0.14 |
| 50 | " | 0.2 | 0.3 | 30 | 0.04 | 9 | 0.13 |
| 51 | M-9 | — | — | 70 | 0.06 | 12 | 0.14 |
| 52 | " | — | 0.3 | 72 | 0.06 | 11 | 0.14 |
| 53 | " | 0.2 | — | 58 | 0.05 | 12 | 0.14 |
| 54 | " | 0.2 | 0.3 | 36 | 0.05 | 11 | 0.13 |
| 55 | M-18 | — | — | 85 | 0.10 | 10 | 0.16 |
| 56 | " | — | 0.3 | 86 | 0.11 | 11 | 0.15 |
| 57 | " | 0.2 | — | 60 | 0.11 | 10 | 0.16 |
| 58 | " | 0.2 | 0.3 | 41 | 0.09 | 9 | 0.14 |
| 59 | M-34 | — | — | 96 | 0.29 | 16 | 0.25 |
| 60 | " | — | 0.3 | 95 | 0.30 | 15 | 0.23 |
| 61 | " | 0.2 | — | 83 | 0.29 | 15 | 0.25 |
| 62 | " | 0.2 | 0.3 | 62 | 0.21 | 13 | 0.22 |

EXAMPLE 6

Six samples of color photographic material were prepared by modifying sample Nos. 32, 33 and 34; namely, the bisphenol derivatives shown in Table 6 were incorporated in the emulsion dispersion in layer 1 in the amounts indicated in Table 6.

As is clear from Table 6, the effectiveness against light discoloration of using anti-discoloration agents in combination with the ether compounds of the present invention was further enhanced by incorporating bisphenolic compounds.

EXAMPLE 7

A paper support coated with polyethylene on both sides was provided with the following seven layers to prepare sample No. 64 (control) of multi-color photographic paper.

Layer 1: containing 1.5 g of gelatin, 0.32 g (as silver) of a blue-sensitive silver chlorobromide emulsion, and 0.3 g of DOP having dissolved therein $1.2 \times 10^{-3}$ mole of a yellow coupler (Y-3) and 0.015 g of HQ-1.

Layer 2: containing 0.9 g of gelatin and 0.06 g of DOP having 0.09 g of HQ-1 dissolved therein.

Layer 3: containing 1.3 g of gelatin, 0.27 g (as silver) of a green-sensitive silver chlorobromide emulsion and

TABLE 6

| Sample No. | Anti-discoloration agent | Ether compound | Bisphenolic derivative | Amount (g) | Light discoloration Discoloration percent | Y-stain |
|---|---|---|---|---|---|---|
| 32 | IV-5 | 40 | — | — | 42 | 0.05 |
| 32-2 | " | " | VIII-4 | 0.05 | 30 | 0.02 |
| 32-3 | " | " | VIII-17 | 0.07 | 27 | 0.03 |
| 33 | " | 45 | — | — | 39 | 0.05 |
| 33-2 | " | " | VIII-4 | 0.05 | 26 | 0.03 |
| 33-3 | " | " | VIII-17 | 0.07 | 21 | 0.04 |
| 34 | " | 4 | — | — | 36 | 0.04 |
| 34-2 | " | " | VIII-4 | 0.05 | 28 | 0.03 |
| 34-3 | " | " | VIII-17 | 0.07 | 22 | 0.04 |

0.2 g of DOP having dissolved therein 0.59×10⁻³ mole of a magenta coupler (M-4) and 0.015 g of HQ-1.

Layer 4: containing 1.5 g of gelatin, and 0.6 g of DOP having 0.5 g of UV-1, 0.3 g of UV-2 and 0.04 g of HQ-1 dissolved therein.

Layer 5: containing 1.6 g of gelatin, 0.3 g (as silver) of a red-sensitive silver chlorobromide emulsion and 0.2 g of DOP having dissolved therein 0.35×10⁻³ mole of C-1, 0.35×10⁻³ mole of C-3 and 0.005 g of HQ-1.

Layer 6: containing 1.2 g of gelatin, and 0.3 g of DOP having dissolved therein 0.25 g of UV-1, 0.15 g of UV-2 and 0.02 g of HQ-1.

Layer 7: containing 1.0 g of gelatin.

Sample Nos. 64 to 68 were also prepared by incorporating an anti-discoloration agent, an ether compound, the combination of the these compounds, and the mixture thereof with a bisphenolic derivative in layer 3 of sample No. 64. For the amounts of the respective compounds, see Table 7.

The so prepared samples were exposed through an optical wedge to a green monochromatic light and subsequently processed as in Example 4. The processed samples were exposed to light in a xenon weather meter (of the same model as used in Example 4) for three different periods, 250 hrs, 500 hrs and 750 hrs. The reflection densities at the magenta dye image areas were measured and the percent discoloration relative to the initial density of 1.0 was determined. The results are shown in Table 7, from which one can see that sample Nos. 67 and 68 had much less discoloration than the control (sample No. 64).

What is claimed is:

1. A silver halide color photographic material that has on a support at least one silver halide emulsion layer containing a non-diffusible coupler, wherein a compound of formula I) and a compound selected from the group consisting of he compounds of the following formulas (IV), (V), (VI) and VII) are incorporated:

$$R_1-O-R_2 \quad \text{(I)}$$

(IV)

(V)

Y-3

C-3

TABLE 7

| Sample No. | Anti-discoloration agent Compound | Amount (g) | Ether compound Compound | Amount (g) | Bisphenolic derivative Compound | Amount (g) | Percent discoloration of magenta dye image 250 hrs. | 500 hrs. | 750 hrs. |
|---|---|---|---|---|---|---|---|---|---|
| 64 | — | — | — | — | — | — | 31% | 75% | 93% |
| 65 | — | — | 51 | 0.18 | — | — | 30% | 73% | 90% |
| 66 | VI-5 | 0.16 | — | — | — | — | 12% | 25% | 39% |
| 67 | VI-5 | 0.16 | 51 | 0.18 | — | — | 4% | 11% | 25% |
| 68 | VI-5 | 0.16 | 51 | 0.18 | VIII-11 | 0.05 | 3% | 8% | 17% |

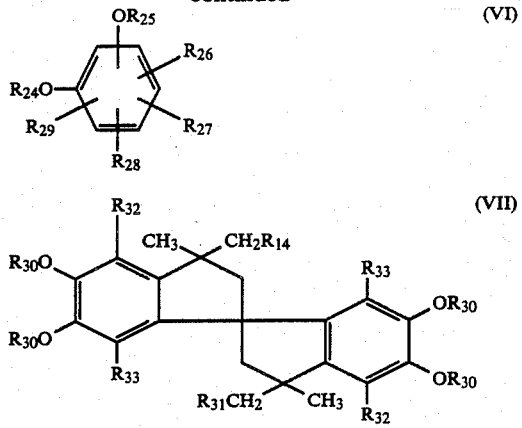

wherein $R_1$ and $R_2$ in formula (I) each represents an alkyl group, a cycloalkyl group or an alkenyl group; $R_{18}$ in formula (IV) is a hydrogen atom, an alkyl group, an aryl group, an alkenyl group, a cycloalkyl group, a heterocyclic group, a trialkylsilyl group, an alkanesulfonyl group, an arylsulfonyl group, —CO—V or —SO$_2$—V (wherein V is an alkyl group, an aryl group, an alkoxy group, an aryloxy group, an alkyloxycarbonyl group or an aryloxycarbonyl group); $R_{19}$, $R_{20}$ and $R_{21}$ are each a hydrogen atom, an alkyl group, an aryl group, an alkoxy group, an aryloxy group or an alkenyl group; and $Z_1$ is a group of non-metallic atoms necessary for forming a 5- or 6-membered ring, said non-metallic atomic group optionally having a substituent;

$R_{22}$ and $R'_{22}$ in formula (V) are each a hydrogen atom, an alkyl group, an alkenyl group, a cycloalkyl group, an aryl group, a heterocyclic group, —CO—V', —SO$_2$—V' or —CONH—V' (wherein V has the same meaning as defined for formula (IV)); $R_{23}$ is an alkyl group, an alkenyl group, an aryl group, an alkoxy group or an aryloxy group; when both $R_{22}$ or $R'_{22}$ and $R_{23}$ are each an alkyl group, $R_{22}$ or $R'_{22}$ may be fused with $R_{23}$ to form a 5- to 7-membered ring; and X and Y are each a hydrogen atom, a halogen atom, an alkyl group, an alkoxy group, an alkenyl group, an aryl group or an aryloxy group;

$R_{24}$ and $R_{25}$ in formula (VI) are each an alkyl group, an alkenyl group, a cycloalkyl group, an aryl group, a trialkylsilyl group or a heterocyclic group; when —OR$_{25}$ is in the position ortho to —OR$_{24}$, $R_{24}$ may be fused with $R_{25}$ to form a 5- or 6-membered ring; and $R_{26}$, $R_{27}$, $R_{28}$ and $R_{29}$ are each a hydrogen atom, a halogen atom, an alkyl group, an alkenyl group, a cycloalkyl group, an aryl group, an acyl group, an acylamino group, an alkylamino group, an alkoxycarbonyl group or a sulfonamido group, provided that not all of $R_{26}$, $R_{27}$, $R_{28}$ and $R_{29}$ are hydrogen atoms at the same time; and $R_{30}$ in formula (VII) is an alkyl group, an alkenyl group, an aryl group, a heterocyclic group, —COR'$_{33}$, —SO$_2$R'$_{33}$ or —CONHR'$_{33}$ (wherein R'$_{33}$ is an alkyl group, an alkenyl group or an aryl group), provided that when $R_{30}$ is an alkyl group, the adjacent $R_{30}$s may be fused together to form a 5- or 6membered ring; $R_{31}$ is a hydrogen atom, an alkyl group, an aryl group or an alkenyl group; and $R_{32}$ and $R_{33}$ are each a hydrogen atom, a halogen atom, an alkyl group or an alkenyl group.

2. A silver halide color photographic material according to claim 1, which contains a compound of formula (IV).

3. A silver halide color photographic material according to claim 1, which contains a compound of formula (V).

4. A silver halide color photographic material according to claim 1, which contains a compound of formula (VI).

5. A silver halide color photographic material according to claim 1, which contains a compound of formula (VII).

6. A silver halide color photographic material according to claim 1, which further contains a bisphenol compound of the following formula (VIII):

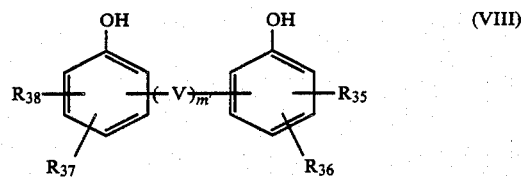

wherein $R_{35}$, $R_{36}$, $R_{37}$ and $R_{38}$ are each a hydrogen atom, an alkyl group or an alkenyl group, provided that at least one of $R_{35}$ and $R_{36}$ and at least one of $R_{37}$ and $R_{38}$ are each an alkyl group; V is —O—, —S— or an alkylene group; and m' is 0 or 1.

7. The photographic material of claim 1, wherein $R_1$ is an alkenyl group.

8. A silver halide color photographic material comprising a support, at least one silver halide emulsion layer containing a non-diffusible coupler on said support, wherein a compound represented by the following formula is incorporated in said silver halide emulsion layer or in a layer adjacent thereto or in both

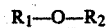

wherein $R_1$ represents an alkenyl group and $R_2$ represents an alkyl, cycloalkyl or alkenyl group.

9. A silver halide color photographic material according to claim 8, which further contains a compound of formula Ib

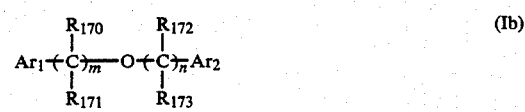

wherein $R_{170}$, $R_{171}$, $R_{172}$, and $R_{173}$ each represents a hydrogen atom, an alkyl group or an aryl group; Ar$_1$ and Ar$_2$ each represents an aryl group; and m and n each represents 1 or 2.

10. A silver halide color photographic material according to claim 8, wherein the alkenyl group represented by $R_1$ has 2 or 3 carbon atoms.

11. A silver halide color photographic material according to claim 8, wherein $R_2$ is an alkyl group.

12. A silver halide color photographic material according to claim 11, wherein $R_2$ has 10 to 28 carbon atoms.

13. A silver halide color photographic material according to claim 9 wherein the alkenyl group represented by $R_1$ has 2 or 3 carbon atoms.

14. A silver halide color photographic material according to claim 9 wherein $R_2$ is an alkyl group.

* * * * *